United States Patent [19]

Correa et al.

[11] Patent Number: 5,397,706

[45] Date of Patent: Mar. 14, 1995

[54] SERUM-FREE BASAL AND CULTURE MEDIUM FOR HEMATOPOIETIC AND LEUKEMIA CELLS

[76] Inventors: Paulo N. Correa, 42 Rockview Gardens, Concord, Ontario, Canada, L4K 2J6; Arthur A. Alexrad, 3 Troon Court, Willowdale, Ontario, Canada, M2P 1N4

[21] Appl. No.: 103,419

[22] Filed: Aug. 6, 1993

Related U.S. Application Data

[63] Continuation of Ser. No. 788,527, Nov. 6, 1991, abandoned.

[51] Int. Cl.$^6$ .............................................. C12N 5/00
[52] U.S. Cl. ........................... 435/240.31; 435/240.2; 435/240.3
[58] Field of Search .............. 435/240.2, 240.3, 240.31

[56] References Cited

U.S. PATENT DOCUMENTS

| | | | |
|---|---|---|---|
| 4,560,655 | 12/1985 | Baker | 435/240.31 |
| 4,675,291 | 6/1987 | Yamamura et al. | 435/240.3 |
| 4,786,599 | 11/1988 | Chessebeuf et al. | 435/240.3 |
| 4,816,401 | 3/1989 | Taupier et al. | 435/240.3 |
| 5,021,349 | 6/1991 | Drouet et al. | 435/240.3 |
| 5,126,261 | 6/1992 | Morris et al. | 435/240.31 |
| 5,155,036 | 10/1992 | Hagiwara et al. | 435/240.31 |

FOREIGN PATENT DOCUMENTS

| | | | |
|---|---|---|---|
| 0205387 | 12/1986 | European Pat. Off. | C12N 5/02 |
| 0304150 | 2/1989 | European Pat. Off. | C12N 5/02 |
| 2196348 | 4/1988 | United Kingdom | C12N 5/02 |
| WO88/02774 | 4/1988 | WIPO | C12N 5/02 |
| WO89/06694 | 7/1989 | WIPO | C12P 15/00 |

OTHER PUBLICATIONS

Monette, F. C. et al., *Exp. Hematol.* 16:250–255, 1988.
Zhou, Yi–Qing et al., *Blood* 82(3):800–806, 1993.
Comptes Rendus Des Seances De L'Academie Des Sciences, Serie III; Sciences De La Vie, Cormier et al., vol. 299, No. 6, Jul. 1984, pp. 143–146.
Chemical Abstracts, Sonoda et al., vol. 109, No. 25, Dec. 1988, p. 632.
Chemical Abstracts, Konwalinka et al., vol. 106, No. 3, Jan. 1987, p. 150.
Blood, Correa et al., vol. 78, No. 11, Dec. 1991, pp. 2823–2833.
International Journal of Cell Cloning, Correa et al., vol. 10, No. 5, 1992, pp. 286–291.
Miura et al, "Proceedings of the Int. Symp. on Growth & Differentiation of Cells in Defined Environment", published 1985, pp. 161–166.
1990 Gibco BRL Catalogue & Reference Guide, published in 1990, pp. 105–107 and 262.
Sawada et al, J. Clin. Invest., 83(5). 1989. pp. 1701–1709.
Konwalinka et al., Exp. Hematol. (N.Y.), 16(2). 1988. pp. 125–130 (Biosis Abstract).
Drouet et al., Br. J. Haematol., 73(2). Oct. 1989. pp. 143–147 (Biosis Abstract).
Yamane, "Nutritional Requirements of Cultured Cells," issued 1978, pp. 1–21.

*Primary Examiner*—Douglas W. Robinson
*Assistant Examiner*—Susan M. Dadio
*Attorney, Agent, or Firm*—Darby & Darby

[57] ABSTRACT

A basal serum-free medium and a hematopoietic cell growth and differentiation-promoting serum-free medium based thereon are provided for the maintenance, cultivation, growth and differentiation of erythroid progenitor cells, other hematopoietic progenitor cells, and leukemia cells in which the effects of various growth factor compounds can be quantitatively evaluated. Both media are wholly serum-free and contain no intrinsic growth factor compounds. The hematopoietic growth and differentiation medium consists essentially of the basal serum-free medium to which has been added at least one primarily but not exclusively growth-promoting agent selected from heme or hemin, interleukin-3 and recombinant human stem cell factor (and optimally all of them), and at least one primarily but not exclusively cell differentiation-promoting agent selected from erythropoietin (Epo), insulin-like growth factor (IGF) and a retinoid (and optimally including all of them).

19 Claims, 12 Drawing Sheets

SERUM-FREE BASAL AND CULTURE MEDIUM FOR HEMATOPOIETIC AND LEUKEMIA CELLS

This is a continuation of application Ser. No. 07/788,527, filed Nov. 6, 1991, now abandoned.

FIELD OF THE INVENTION

This invention relates to culture medium and more particularly to a culture medium for the maintenance and growth of erythroid progenitor cells, other hematopoietic progenitor cells and leukemia cells.

BACKGROUND OF THE INVENTION

Mammalian erythropoiesis is normally regulated in vivo by Epo (erythropoietin), a glycoprotein hormone responsible for the differentiation of red blood cells and for the viability and proliferation of their progenitors. Years after the introduction of culture media for the growth of the erythroid progenitors CFU-E (colony forming unit-erythroid) and BFU-E (burst forming unit-erythroid) it was found that fetal bovine serum (FBS) contained significant quantities of an Epo-like activity.[1] Originally, this was believed to be due to the presence of Epo in FBS, but radioimmunoassays of Epo in FBS found only minute amounts of the hormone.[2,3] Subsequently, it was shown that the Epo-like activity of FBS was abrogated by an antiserum directed against insulin-like growth factor I(IGF-I), but not by anti-Epo antiserum.[3] The same investigators also found that purified human IGF-I could stimulate colony-formation by CFU-E from murine fetal liver and adult bone marrow cells in a "serum free" "SF" medium.[4] Further studies showed that IGF-I enhanced both CFU-E- and BFU-E-derived colony formation from human bone marrow and peripheral blood in "SF" medium as well[5].

To determine the cellular and molecular mechanisms that regulate erythropoiesis, there is needed a truly SF culture system for circulating erythroid progenitor cells which would be defined with respect to all activities that are stimulatory for erythropoiesis. Simple depletion of serum from a culture medium does not necessarily remove from it all undefined serum factors. Major vehicles for the uncontrolled presence of such factors in culture media, in the absence of added serum or plasma, are the albumin preparations commonly employed, most typically Cohn's Fraction V. These have been shown to provide a mitogenic factor(s)[6,7] referred to as BPA ("Burst Promoting Activity"[8]) which has so far remained molecularly unidentified. In fact, most so-called "SF" media in the current literature use bovine serum albumin (BSA) preparations that are known to be contaminated with such activities. Effectively, serum residues provide a "dirty background" which precludes accurate and reliable study of the precise effects of added growth factors. Accordingly, in this specification, the term "serum-free" or "SF" is used in quotation marks in instances where reference is made to a medium reported originally to be serum-free but subsequently discovered to be still serum-contaminated.

In our laboratory, we have previously shown that treatment of BSA with activated charcoal removes its BPA-like activity.[6] Using a fatty-acid-free and globulin-free BSA (FAF, GF BSA) preparation in a SF medium for the growth of BFU-E from bone marrow, Ogawa and co-workers[9] demonstrated that under these stringent conditions, a defined exogenous source of BPA-like activity, interleukin-3 (IL-3) or GM-CSF, had to be added in order to obtain growth of day-14 erythroid bursts. With this SF medium, however, we were unable to grow erythroid bursts or-colonies from circulating progenitor cells.

The study of erythropoiesis, including the study of the growth and proliferation of leukemia cells, so important to the development of understanding and eventual control of this disease, requires the provision of a cell growth medium which ensures optimum growth of the cells under study. It also requires the provision of a cell growth medium free from unknown ingredients which might affect the cell growth characteristics. Only with such a growth medium can the researcher satisfactorily study the effects of other growth-promoting or -inhibiting factors on cell proliferation and differentiation, as well as study the precise effects of toxic molecules.

It is an object of the present invention to provide a novel cell culture medium for hemopoietic and leukemia cells.

SUMMARY OF THE INVENTION

The present invention, from a first aspect, is based upon the provision of a basal serum-free medium (BSFM) for erythroid and other hematopoietic progenitor cells namely a medium in which the cells will not proliferate. By the identification and provision of such a basal serum-free medium, there is provided to the user a medium to which other ingredients may be added for the specific purpose of determining whether or not such ingredients constitute growth and/or differentiation factors for the cells under study. From a second aspect, the present invention provides a growth and differentiation medium which can be optimised for such cells, the medium being constituted by the basal serum-free medium with certain well-defined additives designed to ensure optimum growth and differentiation of the cells therein. With this optimum growth and differentiation medium, the user can test the effects of various compounds on the cell growth and differentiation characteristics of hematopoietic and leukemia cells. The concept of distinguishing between a basal serum-free medium (BSFM) and a cell growth and differentiation medium provides the basis of the present invention.

Thus, according to the first aspect of the invention, there is provided a basal serum-free medium for erythroid and other hematopoietic progenitor cells and leukemia cells, consisting essentially of:

a minimum essential medium;

an effective amount of each of the four deoxyribonucleosides adenine deoxyriboside, thymine deoxyriboside, guanine deoxyriboside and cytosine deoxyriboside;

an effective amount of each of the four ribonucleosides adenine riboside, uridine riboside, guanine riboside and cytosine riboside;

an effective amount of L-glutamine;

an effective amount of deionized, fatty-acid free and globulin-free bovine or human serum albumin or recombinant albumin;

an effective amount of a human or bovine transferrin;

an effective amount of a phosphatidyl choline;

an effective amount of a $C_{16}$–$C_{24}$ unsaturated fatty acid;

an effective amount of a cholesterol;

an effective amount of d-α-tocopherol or an ester thereof;

an effective amount of at least one bio-acceptable antioxidant;

and an effective amount of at least one antibiotic substance effective to protect the cells against stray infections.

According to the second aspect of the present invention, there is provided a serum-free culture medium for the growth and differentiation of erythroid and other hematopoietic progenitor cells and leukemia cells, said medium being free from indigenous cell growth factors but adapted to receive extraneous cell growth influencing materials for determination of the effects thereof on erythroid and other hematopoietic cells and leukemia cells and for attaining optimal growth thereof, said culture medium consisting essentially of:

a basal serum-free medium as defined above;

an effective amount of at least one growth-promoting agent selected from the group consisting of heme or hemin, interleukin-3, and recombinant human stem cell factor;

an effective amount of at least one cell differentiation-promoting agent selected from the group consisting of erythropoietin, insulin-like growth factor, and a retinoid.

It will be understood that the agents referred to as growth-promoting agents may in addition have some cell differentiation-promoting activity, and that the agents referred to as differentiation-promoting agents may also have some growth-promoting activity.

In this novel and improved SF growth and differentiation medium which we have developed, the concentration of each component has been optimized. With it, we have been able to produce erythroid bursts from the mononuclear cells of human peripheral blood with higher efficiencies than those of either the serum-containing or the "serum-free" media reported in the literature. This medium, which uses BPA-free FAF, GF BSA, and defined sources of BPA-like activity, has allowed us to study the effects of various growth factors such as IGF-I upon circulating erythroid progenitors grown in vitro. We have found that IGF-I does not behave as a BPA, inasmuch as it cannot replace IL-3 in the presence of Epo. The effect of IGF-I in this medium was found to be interchangeable with that of Epo, though at higher concentration, thus revealing an Epo-independent pathway for erythropoiesis in vitro by circulating progenitors of the normal human adult. This mechanism, if operative in vivo, may become important under conditions in which endogenous Epo levels are low.

The BSFM provides no complications such as intrinsic presence of substances, in unknown or even trace quantities, which might have cell growth effects, inhibitory or stimulatory, on hematopoietic progenitor cells or leukemia cells. The medium accordingly provides an ideal test medium for evaluation, optimization and development of growth and differentiation factors that act on hematopoietic progenitor and leukemia cells, as well as elucidation of the mechanism whereby they operate.

According to another aspect, the present invention provides a process of determining the effect of a test substance on the growth characteristics of erythroid and other hematopoietic progenitor cells or leukemia cells, which comprises culturing said cells under predetermined, controlled conditions in a serum-free growth and differentiation medium as defined above and to which has been added a predetermined quantity of said test substance, and recording growth characteristics of said cells in the culture medium.

The SF growth and differentiation medium as defined above provides for the optimal growth in vitro of normal human peripheral blood progenitor cells (BFU-E and CFU-E), normal human bone marrow progenitor cells (BFU-E and CFU-E), normal human bone marrow multipotential hematopoietic stem cells (CFU-GEMM), normal human bone marrow granulocyte/macrophage progenitor cells (CFU-GM), peripheral blood erythroid progenitor cells (BFU-E and CFU-E) from patients with polycythemia vera, bone marrow granulocyte/macrophage progenitor cells (CFU-GM) and erythroid progenitor cells (BFU-E) from patients with Diamond-Blackfan anemia, and human polycythemia vera, and B- and T- leukemia cell lines. The growth of certain leukemia cell lines may not require all components of the complete growth and differentiation medium defined above.

BRIEF REFERENCE TO THE DRAWINGS

Figure 4:
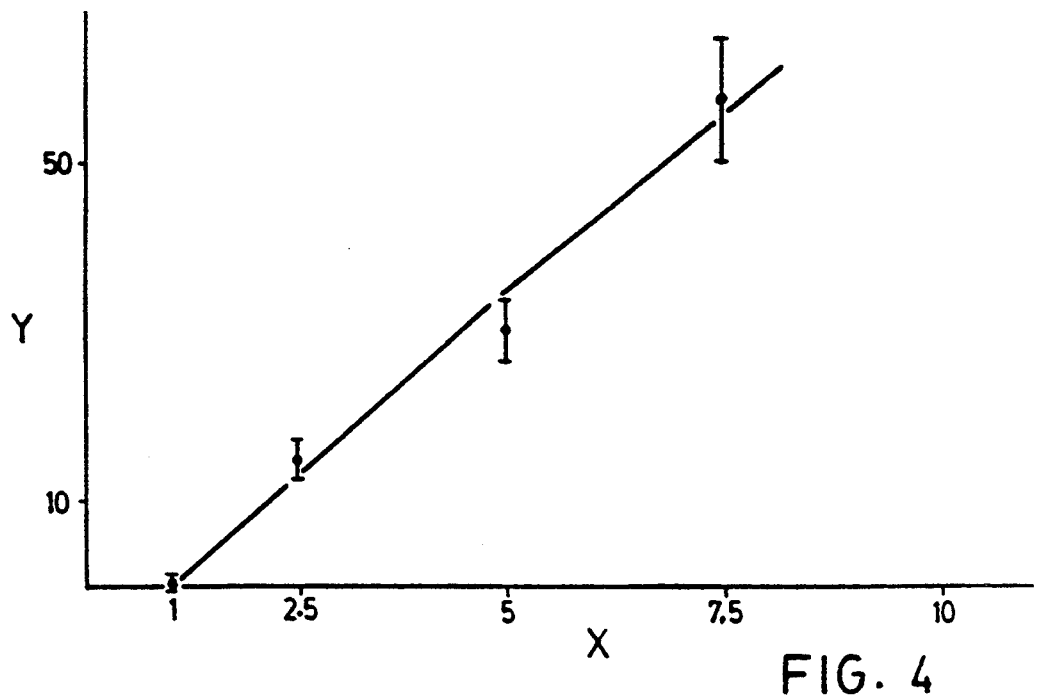
Figure 5:
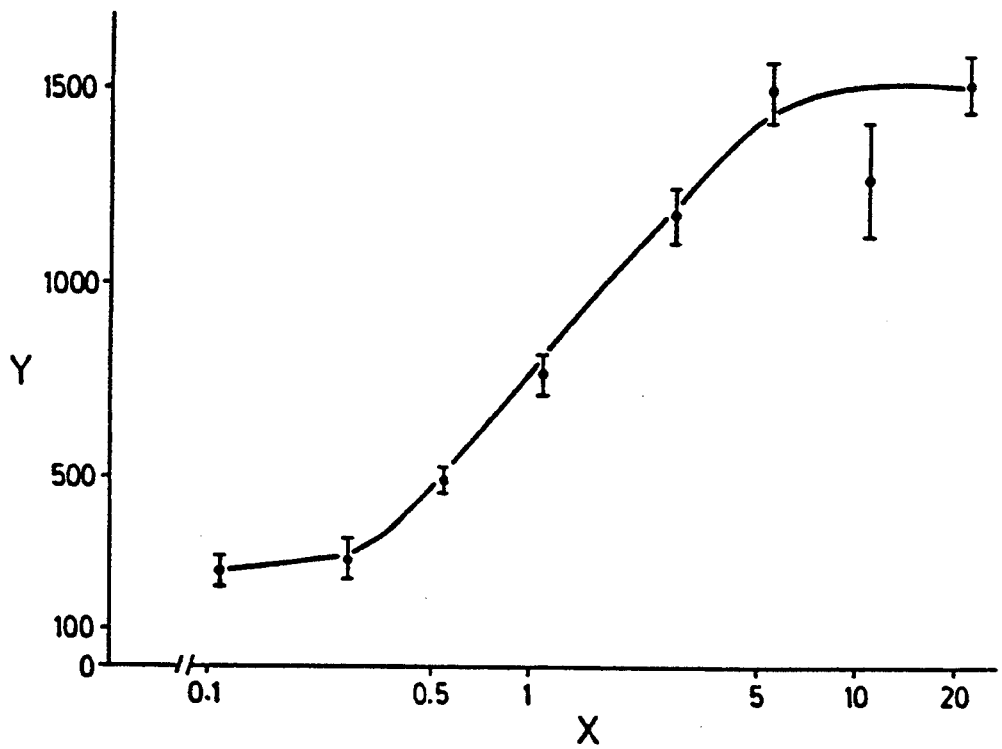
Figure 6:
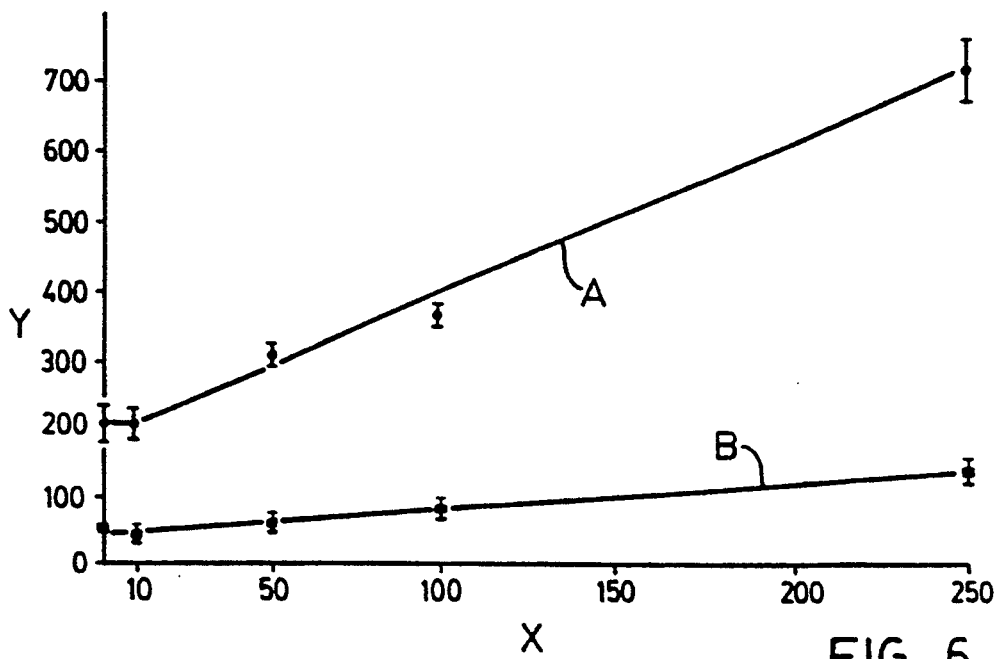
Figure 7:
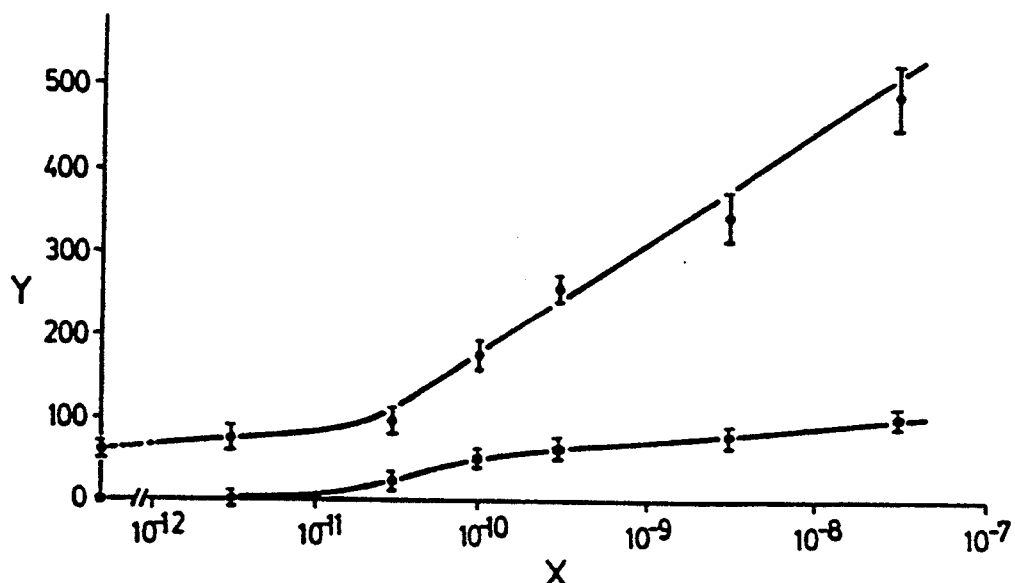
Figure 8A:
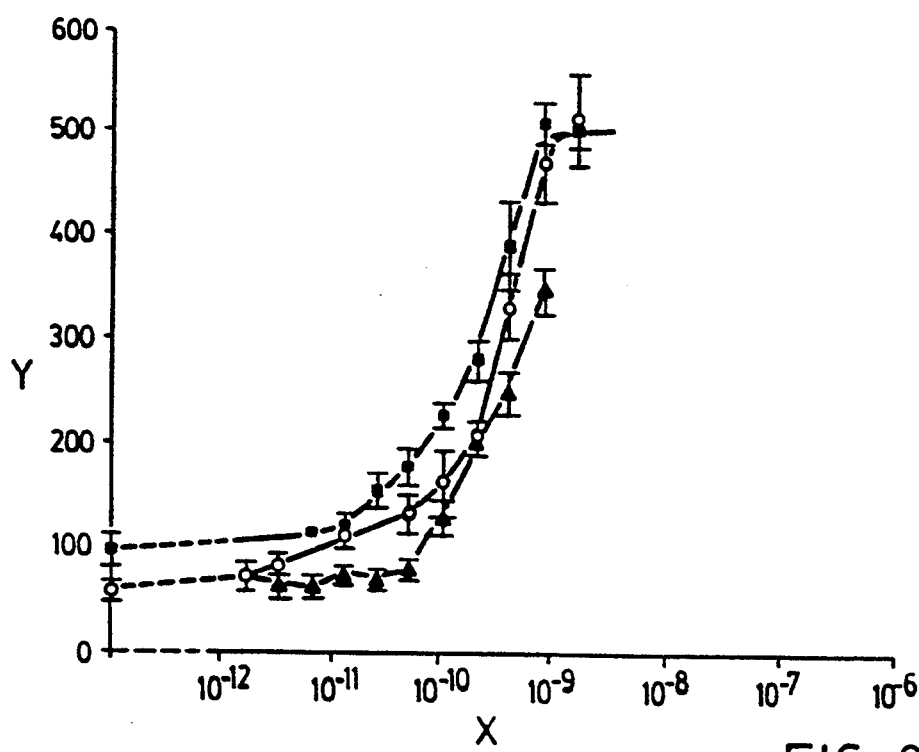
Figure 8B:
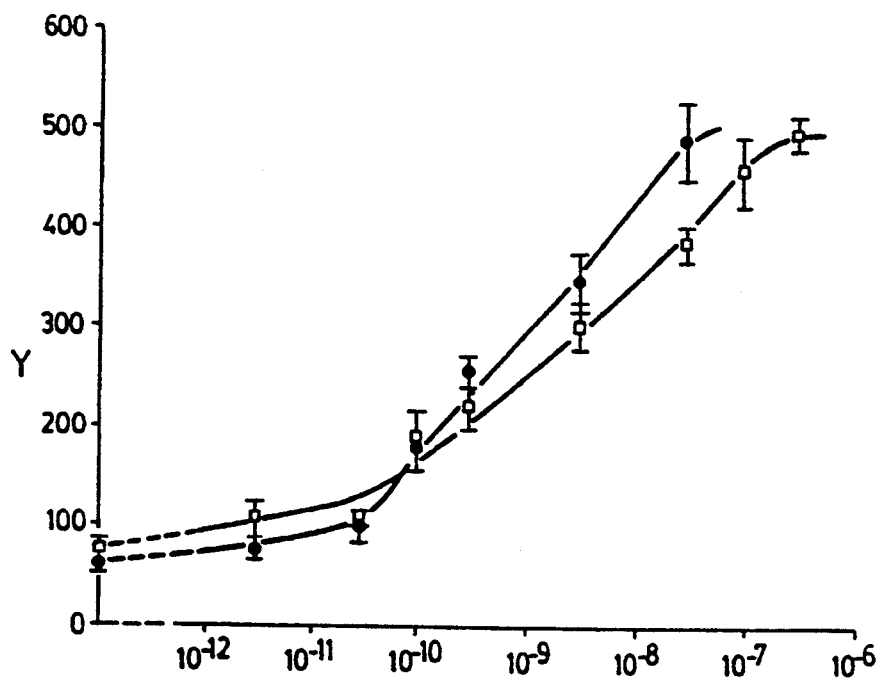
Figure 8C:
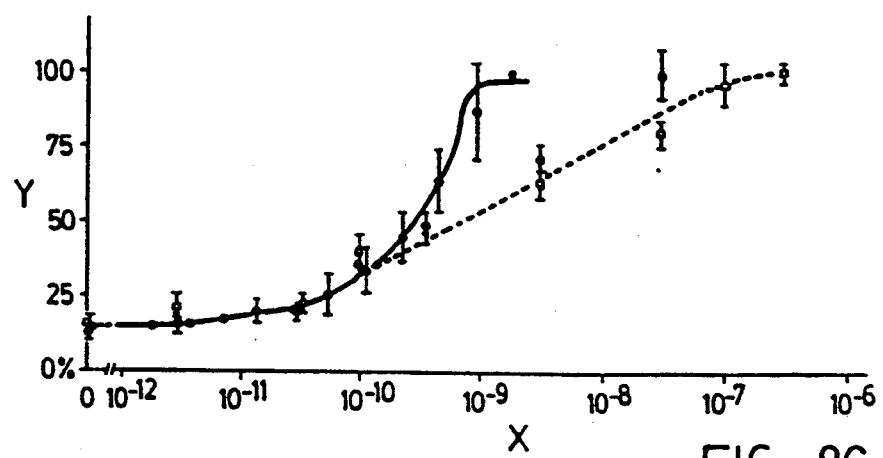
Figure 9A:
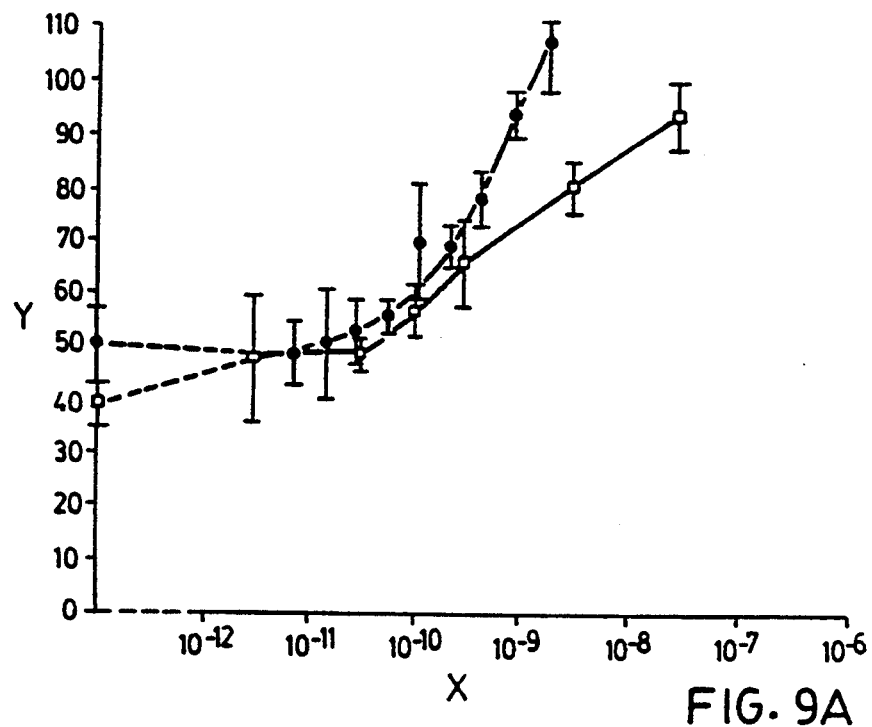
Figure 9B:
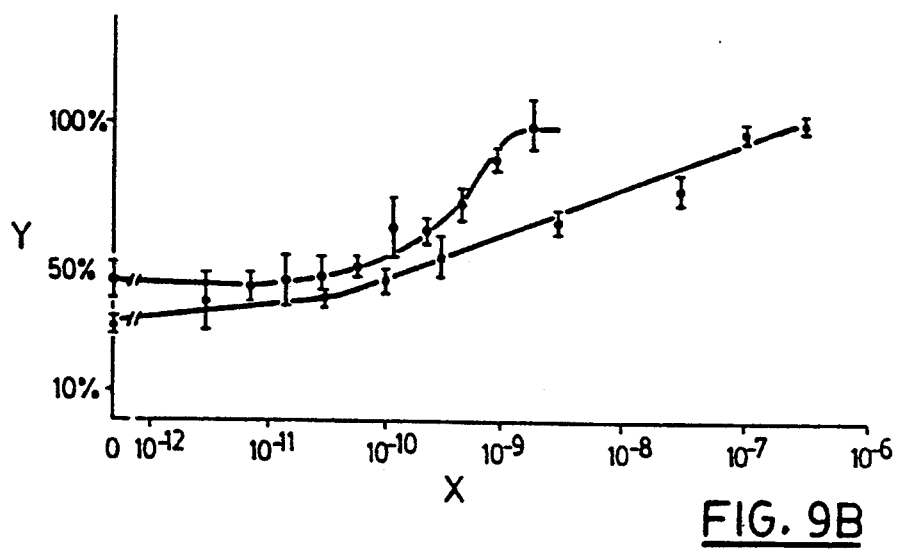
Figure 10:
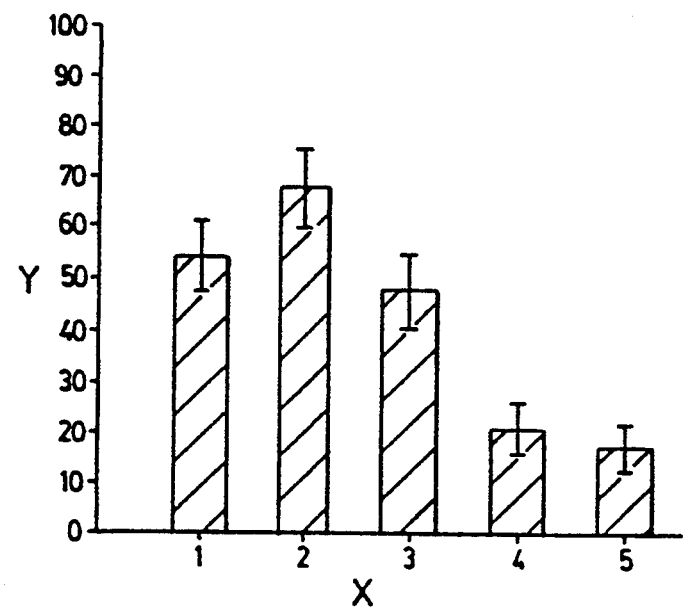
Figure 11:
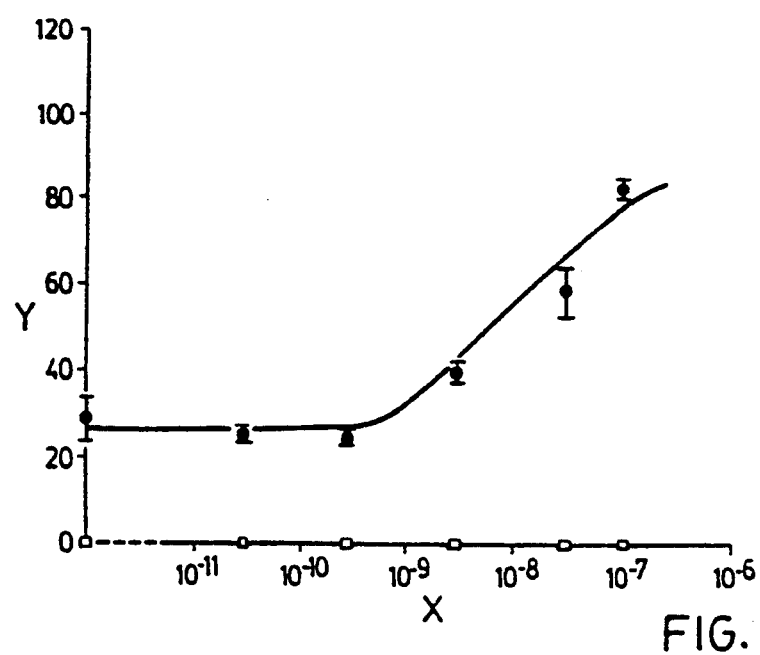

FIG. 4 is a graphical presentation of further results obtained in Example 3 below, namely the relation between number of erythroid bursts produced and number of PB MNC plated in an improved SF medium containing 5.5 ng/ml IL-3, $3 \times 10^{-8}$M retinyl acetate, $3 \times 10^{-8}$M rHu IGF-I, 3.0 U/mL Epo and 0.1 mM hemin;

FIG. 5 is a graphical presentation of the results obtained from Example 4 below. It shows the number of burst-component colonies formed from normal PB MNC in an improved SF medium as a function of rHu IL-3 concentration. Culture medium contained 3.0 U/mL rHu Epo, $3 \times 10^{-8}$M retinyl acetate, $3 \times 10^{-8}$M rHu IGF-I and 0.1 mM hemin FIG. 6 is a graphical presentation of further results obtained from Example 4 below, namely the variation in the number of bursts (■) and their component colonies (o) derived from PB MC as a function of hemin concentration in an improved SF medium containing 5.5 ng/mL rHu IL-3, 3.0 U/mL Epo, $3 \times 10^{-8}$M IGF-I and $3 \times 10^{-8}$M retinyl acetate. Each colony had at least 50 hemoglobinized cells;

FIG. 7 is a graphical presentation of the results obtained from Example 5 below, and shows the number of burst-component colonies derived from PB MNC in an improved SF medium as a function of rHu IGF-I concentration with (o) and without (■) retinyl acetate ($3 \times 10^{-8}$M). The medium contained 5.5 ng/ml rHuIL-3, 3.0 U/mL rHu Epo and 0.1 mM hemin;

FIGS. 8A, 8B, and 8C are graphical presentations of the results obtained from Example 6 below;

FIGS. 9A and 9B are graphical presentations of additional results obtained from Example 6 below, namely comparisons of numbers of erythroid bursts derived from PB MNC as a function of rHu IGF-I or rHu Epo concentration in an improved SF medium, and comparison of normalized values from the above data. Conditions are identical to those of FIG. 8;

FIG. 10 is a graphical presentation of additional results from Example 6 below, namely the effect of the addition of polyclonal anti-Epo antibody HCC-1400 to an improved SF medium with different combinations of rHu Epo and rHu IGF-I. The HCC-1400 antibody was used at 1:50 final dilution; at this concentration it is known to neutralize 6 U/mL of Epo. Molar concentrations of Epo and IGF-I employed were respectively 1.8 nM (6 U/mL) and 300 nM;

FIG. 11 is a graphical presentation of the results obtained according to Example 8 below.

FIGS. 12A, 12B, 12C and 12D are graphical representations of the results of Example 9 below.

Figure 13:
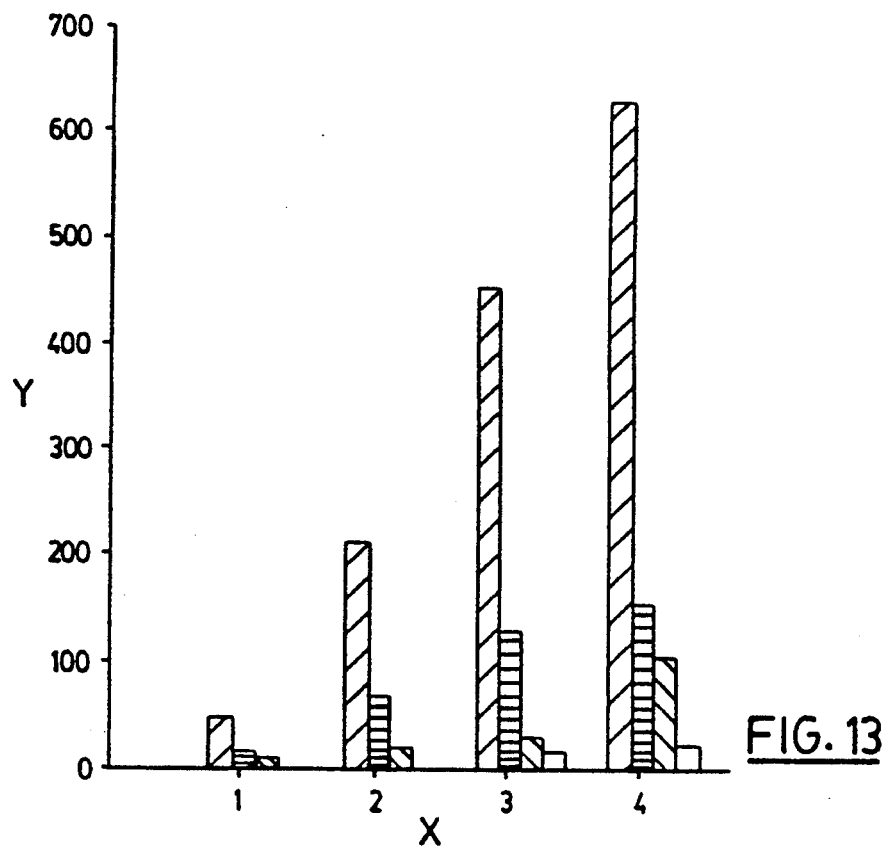

FIG. 13 is a graphical presentation of results obtained according to Example 10 below.

Figure 14:
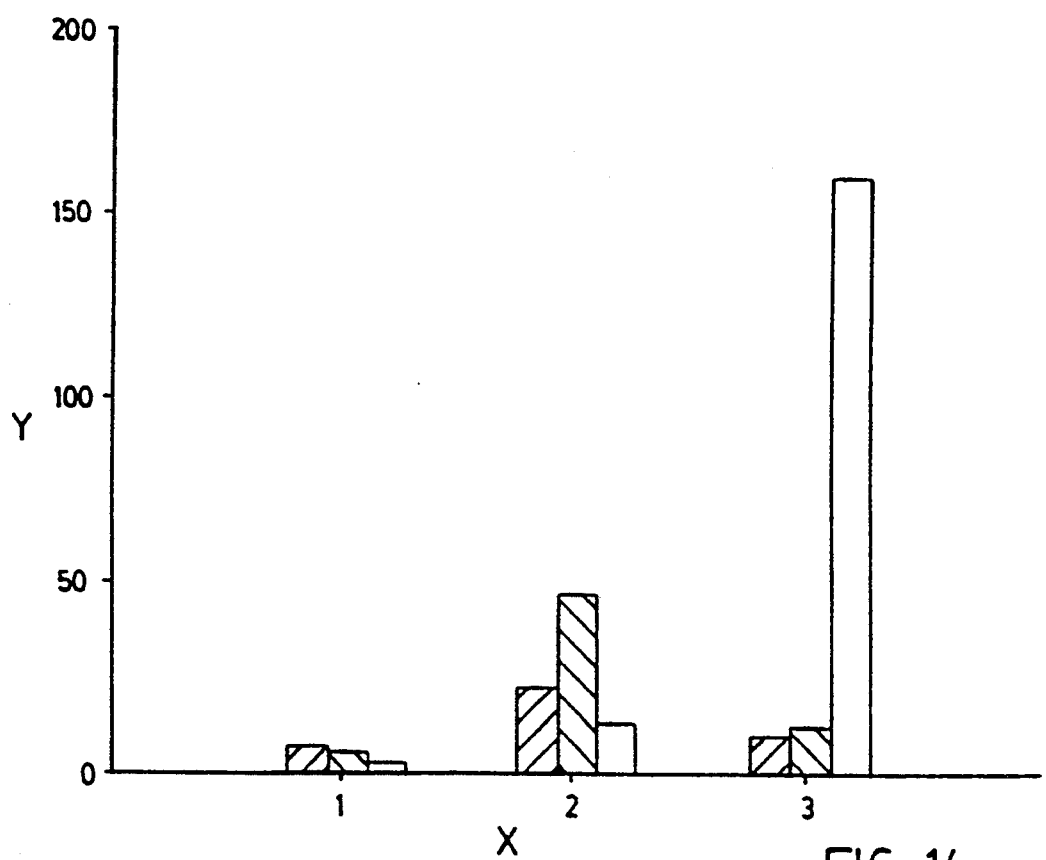

FIG. 14 is a graphical presentation of further results obtained according to Example 10 below.

Figure 15:
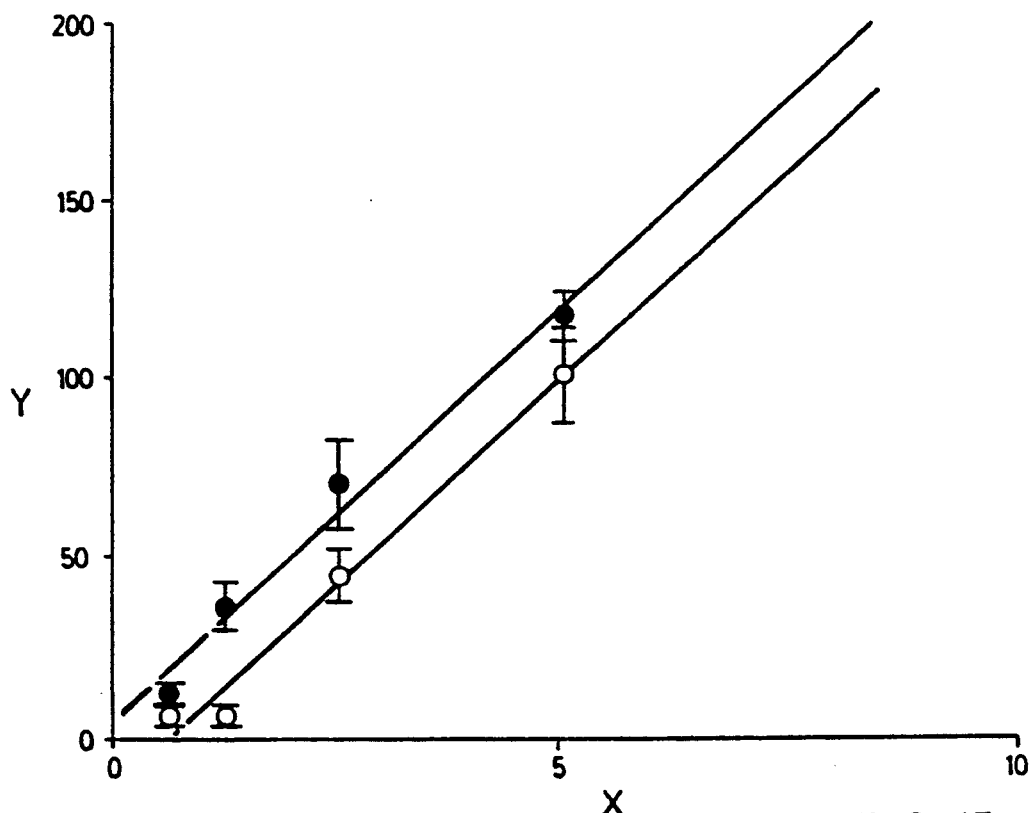

FIG. 15 is a graphical presentation of results obtained according to Example 11 below.

Figure 16:
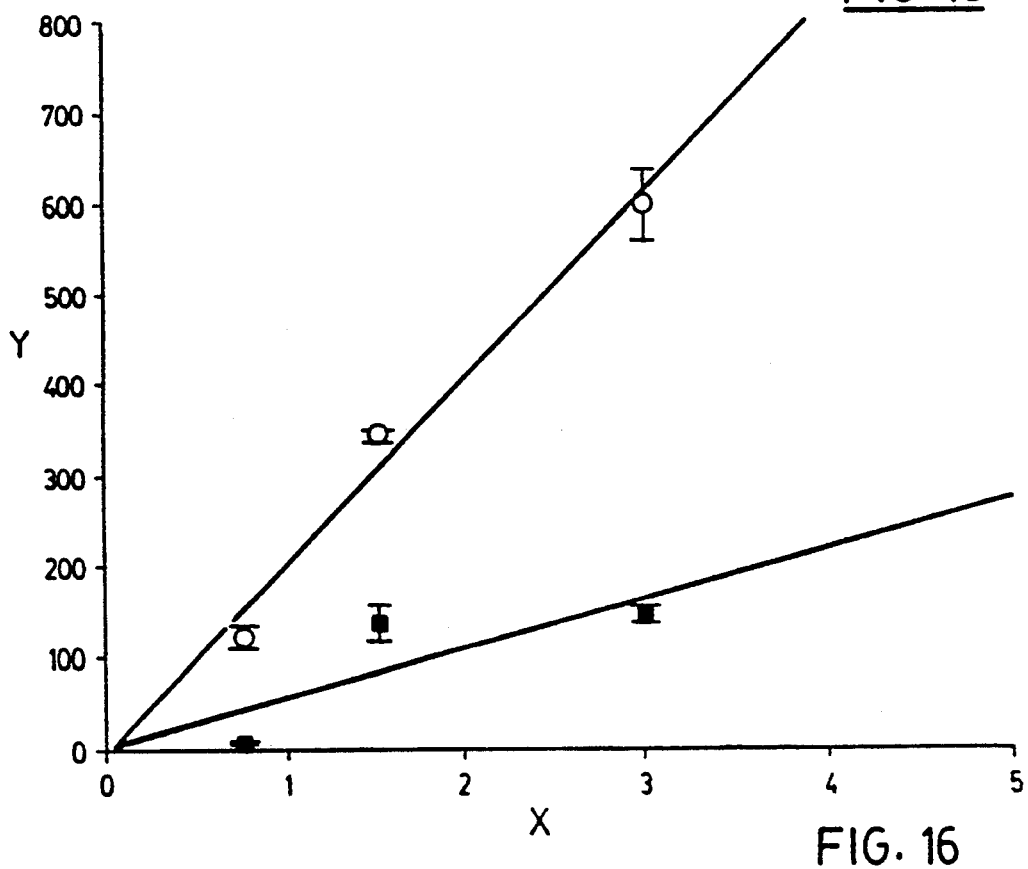

FIG. 16 is a graphical presentation of further results obtained according to Example 11 below.

Figure 17A:
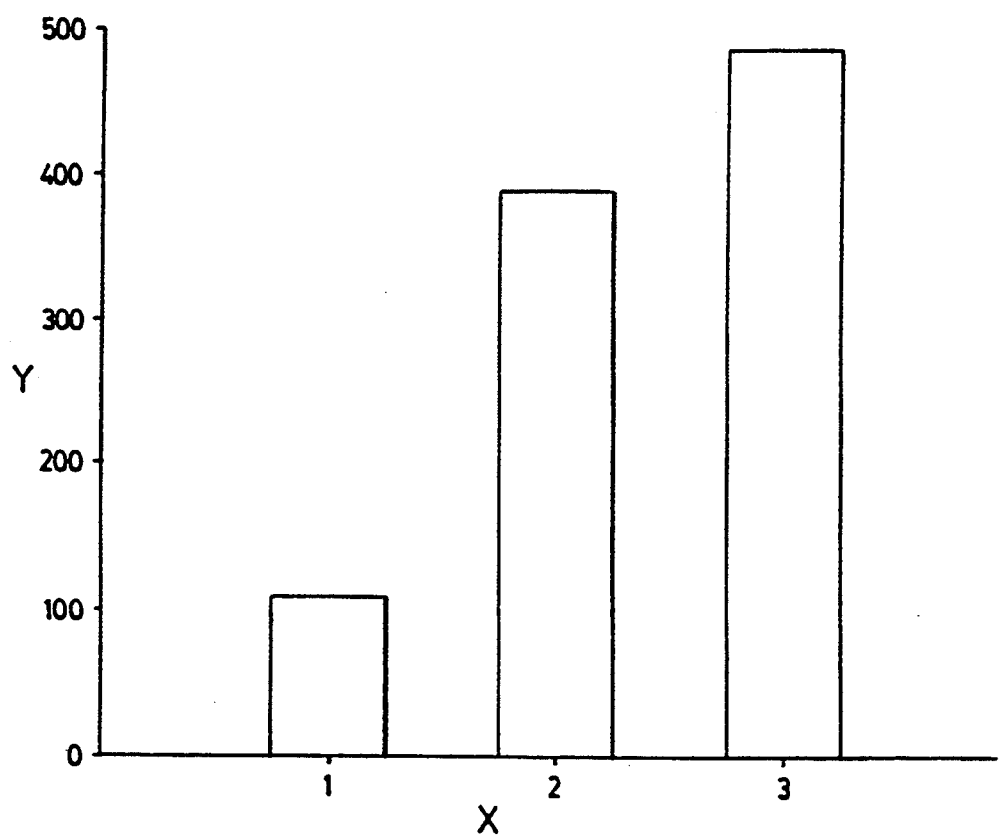
Figure 17B:
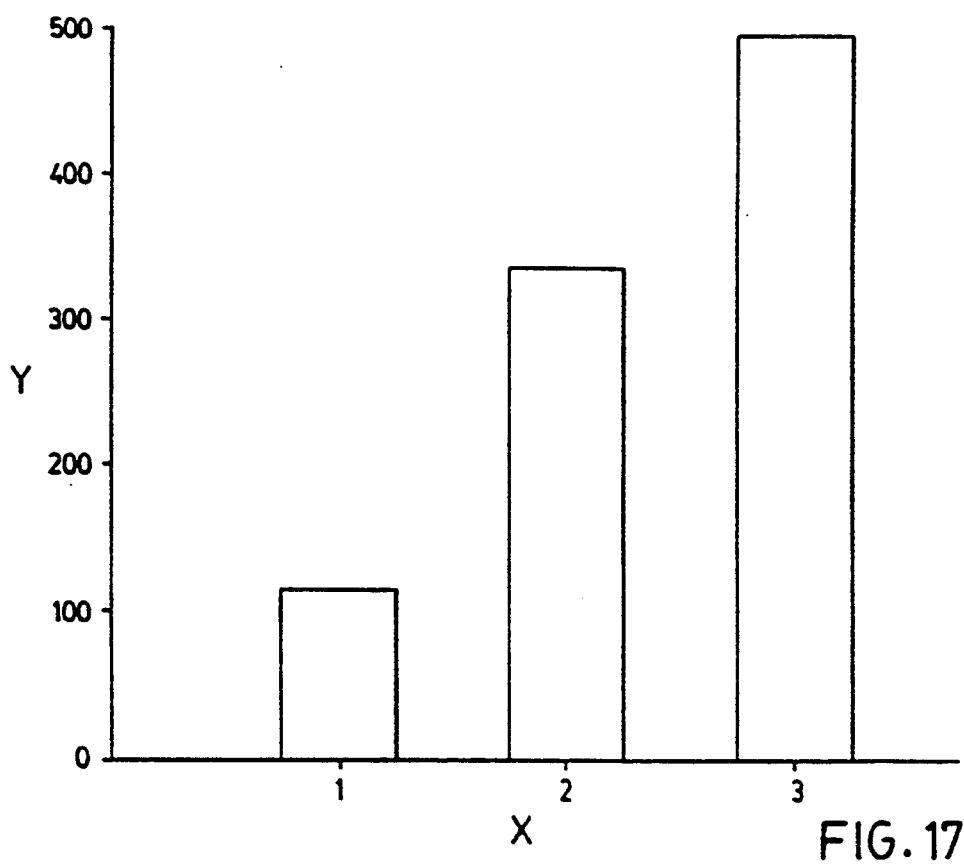

FIGS. 17A and 17B are a graphical presentation of the results obtained according to Example 12 below.

DESCRIPTION OF THE PREFERRED EMBODIMENTS

The basal serum-free medium and the SF growth and differentiation medium as defined above with their minimum number of components provide media in which useful results on cell viability, growth and differentiation, capable of meaningful scientific interpretation can be obtained. According to the preferred embodiments of the invention, however, additional ingredients are added as discussed herein, to produce an optimal SF medium.

The present invention provides a novel improved SF medium for the growth and differentiation of human erythroid progenitor cells from peripheral blood. The activity in this medium of each of its major components has been systematically investigated. It has been found that in the presence of a "clean", fatty acid-free and globulin-free crystallized albumin, rHu IL-3 and rHu Epo were barely sufficient to support the production of erythroid bursts; the bursts were small, developed in minimal numbers, and required benzidine staining for their confirmation. Full maturation of the erythroid bursts necessitated the addition of hemin, which made possible the direct scoring of hemoglobinized bursts in situ. Optimal growth was attained when IGF-I and retinyl acetate were added. It is believed that this is the first SF medium which, using a BPA-free BSA and a defined source of BPA, fully supports the production of bursts in vitro by circulating erythroid progenitor cells from the normal human adult.

Figure 2:
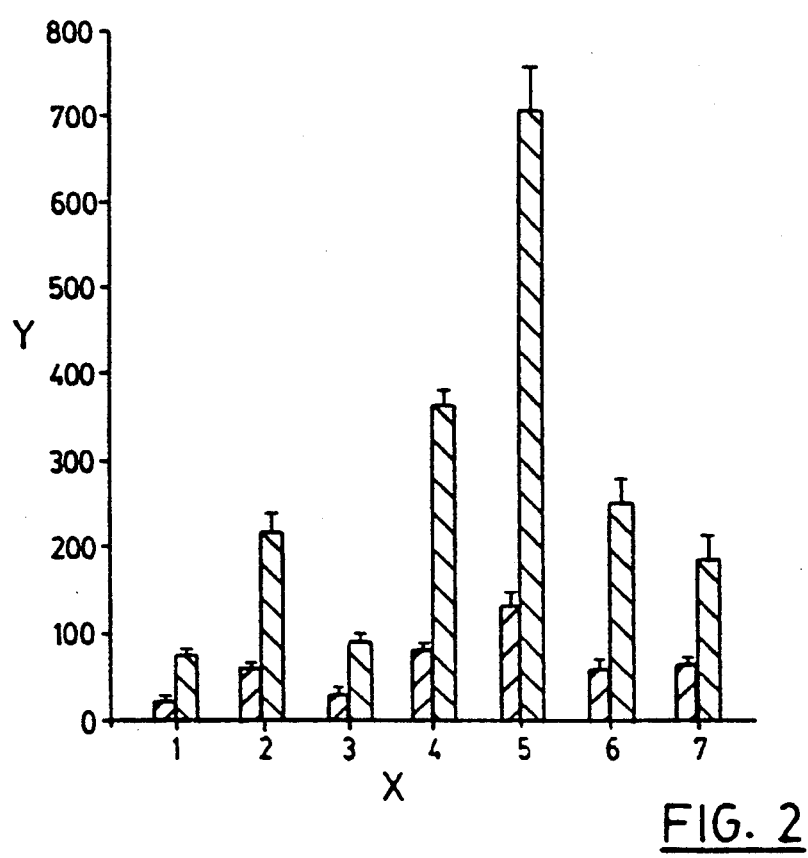
FIG. 2 is a bar graph presentation of the results of Example 2 below, showing variation in the number of erythroid bursts and their component colonies derived from normal human PB MNC with different combinations of hemin and retinyl acetate (in the presence of rHu IL-3, and rHu Epo and rHu IGF-I) in an improved SF medium containing a "clean" BSA and in a serum-containing medium with "dirty" BSA.

It is very important to make the erythroid culture medium completely free of serum products inasmuch as these introduce not only undefined activities that promote growth, but also undefined inhibitory factors, as our results obtained with a "dirty" albumin and serum illustrate in the following examples. A medium containing FBS and Cohn's Fr. V BSA, even after it had been improved by the addition of hemin, retinyl acetate and IGF-1, had a 33-72% lower day-14 colony-forming efficiency than our own improved SF medium. This is demonstrated in Example 2 below, and illustrated in accompanying FIG. 2.

As described above, the first aspect of the invention described and claimed herein comprises basal serum-free medium in which hematopoietic cells will not proliferate. The first component thereof is minimum essential medium, a term well understood by those skilled in the art of cell culturing. Specific preferred examples thereof include $\alpha$ medium, IMDM, and Iscove's modified Dulbecco's medium. Such minimum essential medium is then modified according to the invention to render it specifically suitable for the maintenance of hematopoietic cells and leukemia cells. For this purpose, there are added to it the four deoxyribonucleosides, the four ribonucleosides and the other additives referred to above. The phosphatidyl choline which is used is suitably L-$\alpha$-phosphatidyl choline dipalmitoyl synthetic. The $C_{16}$–$C_{24}$ unsaturated fatty acid is suitably linoleic acid or oleic acid. The cholesterol component is suitably porcine liver cholesterol. The antioxidant is suitably beta-mercaptoethanol or $\alpha$-thioglycerol, or most preferably a mixture of both. One or more antibiotic substances are also included, to protect the medium against infection by airborne or other stray bacteria. Suitable such antibiotics include sodium penicillin G and streptomycin sulphate. Preferably a combination of these two antibiotics is used. The semi-solid matrix material is suitably a carbohydrate such as methylcellulose, agar or agarose, with methyl-cellulose being most preferred.

Suitable relative amounts of the various constituents of the basal serum-free medium are, in final molarity or in grams per milliliter of final volume:

each deoxyribonucleoside: from 1 $\mu$g/mL to 100 mg/mL, and preferably from 5 to 10 mg/mL;

each ribonucleoside: from 1 $\mu$g/mL to 100 mg/mL, and preferably from 5 to 10 mg/mL;

L-glutamine: from 0.1 mM to 20 mM and preferably from 1 to 2 mM;

albumin: from 1 mg/mL to 100 mg/mL and preferably from 10 to 30 mg/mL;

transferrin: from 1 $\mu$g/mL to 1 mg/mL and preferably from 27 to 270 $\mu$g/mL;

phosphatidyl choline: from 0.1 $\mu$g/mL to 100 $\mu$g/mL and preferably from 5 to 10 $\mu$g/mL;

fatty acid: from 0.1 to 100 $\mu$g/mL and preferably from 2 to 10 $\mu$g/mL;

cholesterol: from 0.1 to 100 $\mu$g/mL and preferably from 1 to 10 $\mu$g/mL;

antioxidant: from 1 $\mu$M to 1 mM and preferably from 0.1 to 0.2 mM;

antibiotic: from 0.1 $\mu$g/mL to 250 $\mu$g/mL and preferably from 25 to 100 $\mu$g/mL;

matrix material: from 0.1 mg/mL to 10 mg/mL and preferably from 1 to 3 mg/mL.

In making up the medium for optimal cell growth and differentiation, as determined by the maximum yield of colonies and number of cells per colony over a given period of time, from a given number of cells plated out, in an easily studiable condition, together with a maximized degree of hemoglobinization by the cells, the additional ingredients should be added to the basal serum-free medium, in the following approximate amounts:

hemin or heme: from 50 $\mu$M to 1 mM and preferably from 200 $\mu$M to 500 $\mu$M;

retinoid: from 0.1 nM to 0.1 mM and preferably from 1 mM to 100 nM;

stem cell factor: from 0.5 ng/mL to 1 µg/mL and preferably from 25 to 100 ng/mL;

interleukin-3: from 0.1 ng/mL to 1 µg/mL and preferably from 5 to 25 ng/mL;

erythropoietin: from 0.1 ng/mL to 1 µg/mL and preferably from 10 to 30 ng/mL;

insulin-like growth factor: from 1 pg/mL to 1 µg/mL and preferably from 20 to 100 ng/mL.

Effects of Individual Components of the Growth and Differentiation Medium

BPA: IL-3, HEMIN AND SCF

The problem of providing a defined BPA required for the growth of erythroid bursts has been a major stumbling block in the development of truly SF media. Most recipes are in fact merely serum-deprived media,[5, 10-13] as they call for the use of Cohn's Fr. V BSA, which is known to be contaminated with BPA, as well as lipids, small proteins and other low molecular weight molecules.[13] Delipidation with activated charcoal not only removes lipids but other small molecules as well, and has resulted in the loss of the erythropoietic activity associated with albumin.[6, 7] A source of BPA then had to be provided, either by the addition of leukocyte conditioned media[7] or serum lipoproteins of low to intermediate density.[14]

Figure 1:
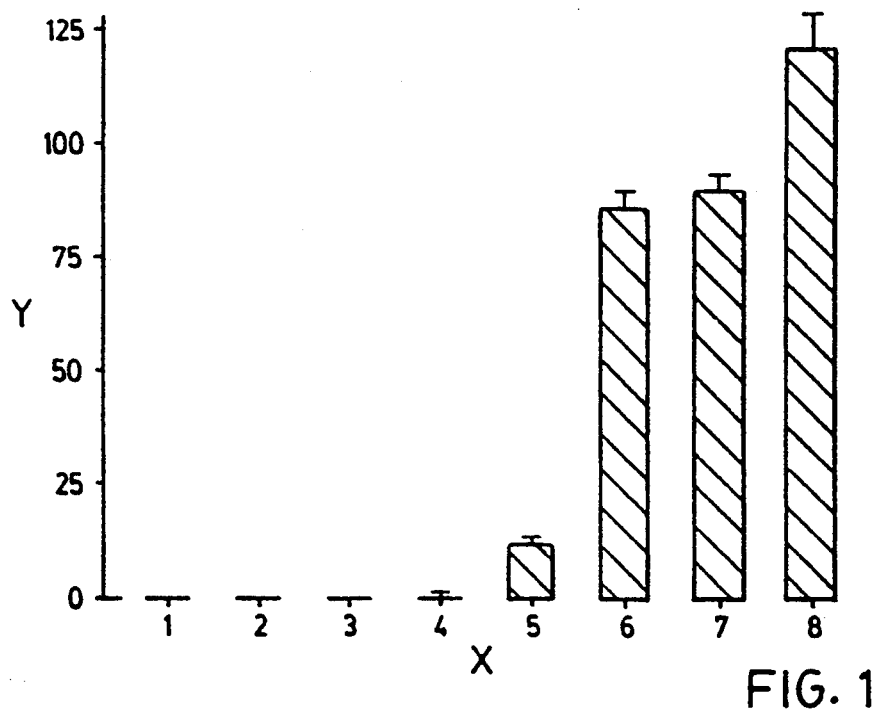
FIG. 1 is a bar graph presentation of the results of Example 1 below.

Investigators have reported BPA-like effects in their media, even though the albumin had been treated with activated charcoal; the source of such BPA was traced to the semi-purified Epo preparations utilized[10] and, when rHu Epo was used, to the accessory cells of bone marrow (monocytes, T-cells, fibroblasts)[7]. It has been reported that accessory cells of bone marrow produce BPA.[7, 15, 17] When we did not remove accessory cells from our PB MNC preparations, as described in Example 1 below, these cells did not appear to provide significant amounts of BPA in our system, judging from the fact that in the absence of added IL-3 and hemin, no bursts developed (FIG. 1).

However, production of erythroid bursts by progenitors among PB MNC was completely abolished by removal of adherent cells in serum-free medium containing IL-3 and hemin but no SCF; addition of rHu SCF partially restored burst formation. Thus either non-adherent erythroid progenitor cells have a requirement for another growth factor(s) normally secreted by adherent cells, or else intimate cell-cell contact interactions between adherent cells and erythroid progenitors are required for burst production.

In our novel culture system we have confirmed the well-documented BPA-like activity of IL-3 for human erythroid growth in vitro; its introduction into our medium as a defined BPA made up for the loss of an undefined BPA resulting from our use of a "clean" BSA preparation and recombinant EPO. In the absence of SCF, the BPA in our SF culture medium appears in fact to be supplied by two defined entities, rHu IL-3 and purified hemin as demonstrated in Example 1 and FIG. 1, and Example 2 and FIG. 2, reported below.

Hemin (iron protoporphyrin IX) is a relatively small (652 dalton) molecule, known to act in the process of normal erythropoiesis. In addition it has distinct proliferative effects in hematopoietic culture. Hemin has been shown to enhance the proliferation of both the multipotential stem cells CFU-GEMM and the early erythroid progenitor cells BFU-E in serum-containing or serum-deprived (i.e. containing undefined BPA's), "SF" cultures of murine and human bone marrow.

Recently, a novel growth factor termed stem cell factor, SCF, has been reported to stimulate primitive pluripotential hemopoietic progenitors in mice[18, 19], rats[20] and humans[18-21]. Several groups have isolated SCF, also termed mast cell growth factor (MGF) and have shown it to be the ligand for the c-kit receptor protein. The product of the c-kit proto-oncogene has tyrosine kinase activity and maps to the mouse W locus on chromosome 5. These findings demonstrated that the genetic anemias of W/W$^y$ and Sl/Sl$^d$ mice were interconnected, with the former having defects in the c-kit receptor and the latter defective production of SCF, the c-kit receptor ligand being the product of the Steel (Sl) locus. Besides the soluble forms of SCF, membrane-bound forms have also been reported[22]. Serum-containing (SC) studies of the effects of SCF on highly enriched, adherent cell-deprived, human bone marrow (BM) BFU-E preparations have shown that it can potentiate primitive hemopoietic colony-formation, and have suggested that it synergises with diverse cytokines, among which are Epo and IL-3[20-21]. No comparable studies exist for human BFU-E from peripheral blood.

The novel serum-free (SF) growth and differentiation medium of the present invention is capable of supporting the growth of circulating erythroid progenitors. However, even though the medium is capable of supporting burst formation at low cell density, removal of adherent cells from the peripheral blood mononuclear cell (PB MNC) suspensions prevents burst formation in SF medium. In accordance with another feature of the present invention, it has been found that recombinant human stem cell growth factor (SCF) can replace the stimulatory activity of adherent cells and thus at least partially restore burst-formation. This is further described in Example 9 below.

IGF-1 AND EPO

The present invention provides strong indications that the effect of IGF-I on burst formation is not limited simply to potentiation of the effect of any Epo that might still be present in the medium. It has been shown that when defined BPAs (IL-3 and hemin) are provided, the basal serum-free medium according to the invention is entirely free of any Epo-like activity capable of inducing erythroid differentiation. Moreover the present work shows that in the presence of an antibody to Epo, IGF-I is fully capable of supporting erythropoietic burst production.

Since experiments according to the present invention were unable to obtain growth of BFU-E with a combination of Epo and IGF-I in the absence of IL-3, hemin, and retinyl acetate, it appears that IGF-I does not have a BPA-like effect upon early BFU-E. This fits with the known incapacity of IGF-I to act as a competence factor, i.e. it cannot recruit quiescent cells into the cell cycle. We have also been able to confirm in our culture system that rHu Epo has no BPA-like activity either.[8]

Thus IGF-I can function in vitro on its own as an erythroid differentiation factor for BFU-E from normal peripheral blood. IGF-I must also function as a growth factor for the progenitors of burst-component colonies. We have found that the cellularity of these colonies was greatly increased by IGF-I whether or not Epo or retinyl acetate were present. This indicates that IGF-I can stimulate cell proliferation within the developing burst, either by promoting self-renewal of the early BFU-E itself, or by targeting progenitor cells that are later in the differentiation sequence than the early BFU-E and promoting their proliferation. The work in support of the present invention appears to represent the first demonstration of Epo-like activity of rHu IGF-I on burst and colony formation from human PB MNC in a demonstrably SF medium.

The SF medium of the present invention provides the opportunity to investigate the sensitivities of human circulating erythroid progenitors to the growth factors that are active in erythropoiesis in vitro. We found that these progenitors required a 100-fold higher concentration of IGF-I than of Epo to reach maximal stimulation (FIGS. 8, 9). We further found that the result of the combined addition of Epo and IGF-I was only partially additive (FIG. 1). The combination of Epo and IGF-I in the presence of IL-3 and hemin gave a greater day-14 colony-forming efficiency than either factor alone, but less than the sum of their separate effects (FIG.1). This observation suggests that there may be two classes of BFU-E-derived erythroid progenitors which overlap with respect to their sensitivities to each of these factors.

The observation that IGF-I (in the presence of IL-3) can completely replace Epo constitutes strong evidence for the existence of an IGF-I-dependent mechanism for proliferation and differentiation of normal circulating BFU-E, which can operate in vitro when Epo levels are low or absent. That such an Epo-independent mechanism might also function in vivo is suggested by the finding that plasma from a patient with chronic renal failure and low Epo levels could nevertheless support erythropoiesis because of its IGF-I content.[23]

Vitamin A

We have found that the addition of Vitamin A (retinyl) acetate or all-trans retinoic acid at physiological concentration[24, 25] (in the absence of Epo) greatly enhances the effect of IGF-I on erythropoiesis in vitro. Even at ineffective concentrations of IGF-I added to the medium, this vitamin is responsible for the expression of a background number of day-14 erythroid colonies, and it synergizes with hemin in stimulating production of increased numbers of these colonies. Retinyl acetate or all-trans retinoic acid thus appears to act as a potentiator of the functions of other growth factors in the SF medium.

The invention is further described for illustrative purposes in the following specific examples, constituting the "Most Preferred Embodiments".

MATERIALS AND METHODS

Cell Preparations

After informed consent, peripheral blood was obtained by venipuncture from healthy donors and was immediately placed in α-minimal essential medium (α-MEM) containing 2% fetal bovine serum (FBS) (#SP80219, Gibco, Grand Island, N.Y.) and 10 U/ml of preservative-free sodium heparin (#820 5077 MF, Gibco). Peripheral blood mononuclear cells (PB MNC) were separated by Ficoll-Hypaque (Pharmacia, Montreal, P.Q.) density-gradient centrifugation at 400×g for 40 min.

Adherent cells were removed by 90 min exposure to the plastic of 50 ml Falcon Tissue Culture Flasks (#3013, Becton Dickinson, Rutherford, N.J.) in the presence of 2% FBS+α-MEM, without agitating the flask at the time of removal of the cell suspension. Cell suspensions were washed three times (400×g, 10 min), the first wash in the presence of 2% FBS+α-MEM, and the subsequent two washes in α-MEM alone. Cell counts were made with the Trypan Blue (0.4%, #630-5250, Gibco) dye-exclusion method.

Clonal Cell Culture

Basal Serum Medium

Serum-free culture of PB MNC was performed with a modification of the technique previously described,[6] in flat bottomed 1.5×1.0 cm plastic wells (#76-000-04, Flow Laboratories, MacLean, Va., now discontinued; Nunclon Delta, Nunc, Roskilde, Denmark, Sl-24 well multidishes-#1-43982 can also be used). Between $5\times10^4$ and $1\times10^5$ PB MNC were plated in 0.5 mL of final culture medium containing α-MEM, 0.8% of 1,500 centipoise methylcellulose (Methocel A4M, premium grade, Dow Chemical Co., Midland, Mich.), 1% fatty acid- and globulin-free crystallized BSA I(Sigma) which was subsequently deionized with analytical grade Ion Exchange Resin (AG 501-X8(D), BioRad Labs, Richmond, Calif.), $2\times10^{-4}$M β-mercaptoethanol (BDH Biochemicals, Poole, England), 270 μg/mL fully iron-saturated bovine transferrin (Sigma), $7\times10^{-7}$M d-α-tocopherol (Clinic Products, Windsor, Ont.), 8 μg/mL L-α-phosphatidyl choline dipalmitoyl synthetic (Sigma), 5.6 μg/mL oleic acid (Sigma), 7.8 μg/mL porcine liver cholesterol, grade 1 (Sigma), 10 μg/mL of each of the four deoxy- and ribonucleosides (Sigma), 2 mM L-glutamine (Sigma), 100 U/mL penicillin G and 50 μg/mL streptomycin sulfate (Gibco) (this combination of ingredients constituting a specific example of a basal serum-free medium according to the invention).

Recombinant and Other Growth and Differentiation Factors

*E. coli*-derived recombinant human somatomedin-C (referred to as rHu IGF-I) having the natural amino acid sequence was purchased from Amersham, Oakville, Ont., or from AMGen, Thousand Oaks, Calif. The recombinant human preparations of erythropoietin (rHu Epo) and Interleukin-3 (rHu IL-3) were from AMGen. Bovine type 1 hemin (ferric chloride protoporphyrin IX) was purchased from Sigma (#H-2250), with ~97% purity by spectrophotometric assay. Retinyl acetate was from Nutritional Biochemicals Corp., Cleveland, Ohio. Recombinant human SCF was a gift from Dr. A. Bernstein (S. Linenbeld Research Inst., Ont.). The final concentrations of these growth and differentiation factors used in the optimal medium were as follow: rHu IGF-I 0.26 μg/mL to 2.6 μg/mL ($3\times10^{-8}$ to $3\times10^{-7}$M), rHu Epo 3.0 U/mL (27 ng/mL, $9\times10^{-10}$M), rHu IL-3 5.5 ng/mL ($2\times10^{-10}$M), rHu SCF 100 ng/mL (3 nM), retinyl acetate or all-trans retinoic acid $3\times10^{-8}$M, and hemin 65.2 or 163.0 μg/mL (1.0 or $2.5\times10^{-4}$M).

Petri dishes containing the wells were incubated at 37° C. in a humidified atmosphere and 5% $CO_2$ for 7 to 9 days for erythroid colonies and 14 to 16 days for erythroid bursts. All erythroid colonies and bursts were scored by in situ observation with an inverted microscope.

Anti-Epo Antibody

Polyclonal rabbit anti-Epo antibody HCC-1400 was obtained from Terry Fox Laboratory, Vancouver, B.C., and used at a final dilution of 1:50, at which concentration it neutralizes 6 U/mL of human Epo.

Criteria cor Scoring of Erythroid Colonies and Bursts

An erythroid burst is defined as either a single colony or a cluster of "burst-component" or "day-14" colonies, each having at least 50 hemoglobinized cells, scored at days 14 to 16 of growth. Hemoglobinized colonies with <50 cells and separated from one another could also be observed; even when they appeared to belong to a single burst, their counts were not included in the counts of bursts. Contiguous colonies which collectively comprised at least 50 cells were scored as a burst. Burst-component colonies, also referred to as "day-14 colonies" or "subcolonies", were easy to count and their numbers could be considered reliable even when crowding of the cultures made the distinction between individual bursts questionable.

EXAMPLE 1

Comparison of the Effects of rHu Epo and rHu IGF-I in the Presence or Absence of rHu IL-3 and Hemin In the initial experiments, we examined the effects growth of several growth factor permutations upon the of erythroid day-14 burst-component colonies from PB MNC. Accompanying FIG. 1 presents the results graphically. On FIG. 1, triplicate or sextuplicate determinations from one or several experiments are expressed as Means ± S.E. FAF, GF BSA (1%) present together with the entirety of the basal serum-free medium components as described under "Clonal Cell Culture" above, was unable, by itself, to support the development of burst-component colonies (FIG. 1, bar 1) and the same negative result was obtained when Epo was added (FIG. 1, bar 2), confirming that the BSA preparation employed was operationally devoid of a BPA-like activity and that the basal serum-free medium by itself does not support growth of primary hematopoietic cells. Hence, in order to obtain burst-formation we would need to add an exogenous source of BPA to the medium. The same results showed that the recombinant Epo preparation was equally devoid of a BPA contaminant, which is often present in semi-purified Epo preparations.[10] This contrasted with the results obtained when rHu Epo alone was added to Cohn's Fr. V BSA (1%). Under these conditions 18±2.5 single-colony bursts developed per $2 \times 10^5$ cells. However, the results thus obtained with Fr. V BSA were erratic, suggesting that this source of albumin has variable quantities of contaminating BPA and may, at times, have none, at least operationally.

The addition of a defined, exogenous BPA-like activity in the form of 5.5 ng/mL of rHu IL-3 was also unable to promote erythroid burst-formation in the absence of any added Epo (FIG. 1, bar 3), demonstrating that the BSA employed is also devoid of an Epo-like activity. In fact, examination of these cultures showed the presence of morphologically erythroid-like colonies that failed to mature, along with granulocytic and monocytic colonies. The addition of 0.1 mM hemin to this basal level of IL-3 did not elicit erythroid differentiation of these colonies either (FIG. 1, bar 4), and addition of rHu Epo and rHu IL-3 showed the presence of a few day-14 erythroid colonies (or single-colony bursts) scorable only with acid benzidine (FIG. 1, bar 5). Addition of 0.1 mM hemin to the combination of Epo and IL-3 dramatically increased the colony-forming efficiency (7-fold, FIG. 1, bar 6). Under these conditions, colonies could now be scored directly in the microscope by their orange colour alone. A comparison of bars 6 and 7 in FIG. 1 shows that, in the presence of hemin and IL-3, addition of IGF-I could effectively replace Epo with respect to burst formation. However, when Epo and IGF-I were added together (at the previously established concentrations), their combined effect was greater than that obtained with either factor alone, but less than the sum of their separate effects (FIG. 1, bar 8).

EXAMPLE 2

Optimization of Serum-Free Culture Conditions

It was reported in 1982 that some retinoids can significantly increase erythroid burst formation.[26] Hence, in order to improve the efficiency of the medium, we tested the effects of combining hemin and retinyl acetate with the full complement of recombinant factors, Epo, IL-3, and IGF-I, except for SCF. We had in this medium previously found that, by themselves, retinyl acetate and all-trans-retinoic acid also had an Epo-like activity, in that they appeared to function as differentiation factors.[27, 28] FIG. 2 also shows that with respect to numbers of burst-component colonies, the effect of a combination of hemin and retinyl acetate (bar 4-bar 1) was significantly greater than the sum of their separate effects [(bar 2-bar 1)+(bar 3-bar 1)], suggesting a synergism, but this effect was not detectable for bursts (bar 4-bar 1) vs [(bar 2-bar 1)+(bar 3-bar 1) ].

Together, hemin and retinyl acetate induced a 4.8-fold increase in the number of burst-component colonies and a 3.5-fold increase in the number of bursts. This contrasts with a 2.8-fold increase in burst-component colonies and a 2.6-fold increase in bursts obtained by stimulation with retinyl acetate only. However, in the presence of serum (10% FBS) and a "dirty" BSA (Cohn's Fr. V), no synergism was apparent (FIG. 2, bars 6a and 7a for bursts, and 6b and 7b for colonies). The highest number of burst-component colonies in serum was significantly lower than that in SF medium (bar 6 vs bar 4), suggesting the presence of inhibitory factors in serum.

Figure 3:
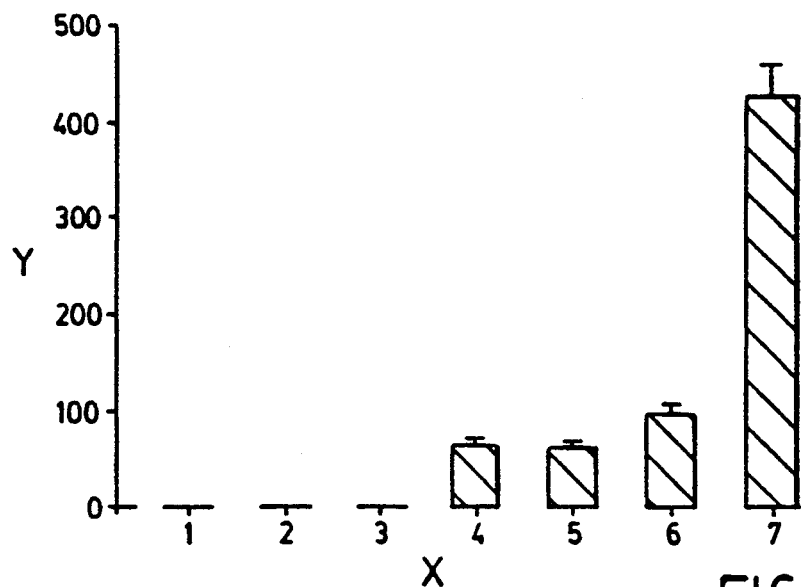
FIG. 3 is a bar graph presentation of the further results of Example 2 below, and illustrating the effect of ATRA on early erythroid colony formation by circulating progenitors in an improved SF medium.

Similar results have been obtained with hemin together with all-trans retinoic acid ATRA (FIG. 3).

To find out whether ATRA behaves in the same way as retinyl acetate, we substituted ATRA for RA (at 30 nM) in the same SF medium. We found that in the absence of any added BPA-like activity (IL-3 or hemin) and of any Epo-like activity (Epo or IGF-I), ATRA was not capable by itself of supporting early colony growth and differentiation (FIG. 3, bar 1). In the presence of Epo, the normal regulator of erythireporetic differentiation, ATRA did not provide a BPA-like activity in that no day-16 colony formation was detected (FIG. 3, bar 2). In the presence of rHu-IL-3, erythroid colonies could be morphologically recognized but no hemoglobinization could be detected (FIG. 3, bar 3). Substituting optimal concentrations of Epo and IGF-1 for ATRA (on an IL-3 background) yielded a comparable number of day-16 colonies (not significantly different from bar 5, FIG. 3; t=2.46 for 2 degrees of freedom and p >0.05) and a much stronger degree of hemoglobinization (FIG. 3, bar 6); still, other erythroid-like colonies could be observed which had not matured. However, colony maturation was dramatically increased when ATRA was added to complete the SF medium (FIG. 3, bar 7), as it induced a 4-fold increase in the number of hemoglobinized d16 colonies. These findings show that ATRA functions in a manner analogous to RA, and strongly suggest that these retinoids act as essential co-factors of erythroid differentiation.

EXAMPLE 3

Cell-Dose Response in an Improved SF Medium

The relation between the number of bursts produced and the number of PB MNC plated was investigated. The results in FIG. 4 show that, in the presence of 5.5 ng/mL of rHu IL-3, 3.0 U/mL rHu Epo, $3 \times 10^{-8}$M IGF-I, 0.1 mM hemin and $3 \times 10^{-8}$M retinyl acetate, the number of bursts varied linearly with the cell concentration between 1 and $10 \times 10^4$ cells/0.5 mL plated. The regression line relating these variables extrapolated through a point not significantly different from the origin, suggesting that the medium is performing satisfactorily for burst production. The efficiency of burst-production was approximately 1 burst/1,300/PB/MNC plated.

EXAMPLE 4

BFU-E Required for rHu IL-3 and Hemin in the Improved SF Medium

A titration of rHu IL-3 (FIG. 5) in the SF medium showed that the number of day-14 burst-component colonies varied linearly with the log of rHu IL-3 concentration. In the absence of added IL-3, no bursts could be detected; the erythroid colonies that were present had a soft orange colour and had <50 cells. At IL-3 concentrations of up to 0.28 ng/mL, hemoglobinized bursts were practically absent, but burst-component colonies could still be recognized by their morphology and a faint orange colour, even though their number and the cellularity of each colony were very low. Between 0.28 and 5.5 ng/mL, colony numbers increased, they had a mean cellularity of about 100 cells/colony, and a few, much larger colonies could also regularly be observed. A plateau of activity was reached at 5.5 ng/mL of rHu IL-3, without any toxic effects. From these data, we chose to use 5.5 ng/mL of rHu IL-3 as our standard concentration of added BPA-like activity for the improved SF medium.

In the improved SF medium, hemin facilitated visualization of hemoglobinized colonies by increasing the intensity of their colour: at 10 $\mu$M, hemin did not increase the number of bursts or their colonies (FIG. 6), but conferred on them a stronger hemoglobinization, their colour now being a definite orange instead of the soft, pale orange colour of the colonies present in the absence of hemin; at 100 $\mu$M hemin, the colonies became redder, and at 250 $\mu$M they seemed to attain a maximal degree of redness. Besides this qualitative effect, which greatly facilitated in situ scoring, both the number of day-14 bursts and the number of day-14 burst-component colonies increased linearly with increasing hemin concentration between 10 and 250 $\mu$M (FIG. 6). Over this range, the number of day-14 burst-component colonies increased 4-fold and the number of day-14 bursts increased 2-fold. The optimal concentration of hemin for both maximal hemoglobinization and number of day-14 bursts and their component colonies derived from $10^5$ PB MNC was 250 $\mu$M. At this cell density, the 500 $\mu$M concentration of hemin was too high for purposes of colony and burst enumeration; colony growth became practically confluent as early as day-12, and by day-14 some lysis was detectable. Still higher concentrations tested (1 mM) were toxic and resulted in widespread lysis of cells in the colonies.

EXAMPLE 5

Titration of rHu IGF-I in the Absence of Epo, with and without Retinyl Acetate

Next, we titrated the number of burst-component colonies against rHu IGF-I concentration, in the absence of Epo or retinyl acetate (FIG. 7). At low concentrations ($<10^{-10}$M), the number of erythroid burst-component colonies was significantly lower than would have been expected if we extrapolated back the linear component of the response curve between $10^{-10}$ and $3 \times 10^{-10}$M IGF-I (FIG. 7, lower curve, closed squares). This suggests that a threshold concentration of IGF-I may be necessary for erythroid burst-component colony formation to be detected. Titration of burst-component colonies against rHu IGF-I concentration, using the same PB MNC but performed in the presence of retinyl acetate (also without Epo), showed that the effect of IGF-I was proportional to the log of its molarity, between $3 \times 10^{-11}$ and $3 \times 10^{-8}$M, without having reached a plateau of activity at the highest concentration tested (FIG. 7, upper curve, closed circles). Accordingly, the half-maximal stimulation must be $>3 \times 10^{-10}$M ($>2.6$ ng/mL). At $3 \times 10^{-12}$M, rHu IGF-I appeared to be ineffective against a background of early erythroid colonies which were apparently promoted by the presence of the retinoid at a concentration of $3 \times 10^{-8}$M. Once again, retinyl acetate at the highest effective concentration greatly enhanced ($\sim$5-fold) the number of burst-component colonies scored.

EXAMPLE 6

Comparison of the Titration of rHu Epo and rHu IGF-I Under Optimal SF Conditions for Burst-Production The effects of either Epo or IGF-I on the production of burst-component colonies, each titrated in the improved SF medium, but in the absence of the other GF, were compared. The results are expressed as raw data (FIGS. 8A and 8B) and as percentage of the maximal stimulation observed with each GF (FIG. 8C). The Epo dose-response curve (continuous line joining the closed circles) is the mean of 3 separate experiments from different donors. Epo in our medium showed the familiar type of dose-response curve, plateauing at 3–6 U/mL or $9-18 \times 10^{-10}$M (Epo mol. wt. 34,000). Below $2 \times 10^{-11}$M rHu Epo, the number of burst-component colonies lay within the background level induced by retinyl acetate alone, in the absence of any Epo or IGF-I. From this normalized Epo curve, the half-maximal stimulation of the hormone upon burst-component colony formation was $2.7 \times 10^{-10}$M (0.89 U/mL), which corresponds to an Epo protein concentration of 8.1 ng/mL.

A rHu IGF-I titration from 2 experiments with different donors is also shown in FIG. 8B (one in closed circles, the other in open squares). Each is expressed both as raw data (FIG. 8B) and as a percentage of its own maximal effect (FIG. 8C). It is apparent that the concentration of rHu IGF-I needed to reach maximal activity (at $10^{-7}$M) is nearly two logs of molarity higher than what we have observed with Epo in the same medium. Between $3 \times 10^{-11}$ and $3 \times 10^{-7}$M rHu IGF-I, the number of burst-component colonies varied proportionately with the log of IGF-I concentration, its half-maximal stimulation lying around $6.5 \times 10^{-10}$M IGF-I, which corresponds to a protein concentration of 5.6 ng/mL. It is worth remarking that the overall numbers of burst-component colonies obtained by stimulation with each growth factor alone, as seen at plateau concentrations, were not significantly different from one another (a range of 462 to 503 colonies/$10^5$ MNC for all 5 experiments).

Titration of rHu Epo and rHu IGF-I expressed in terms of the number of bursts produced (FIG. 9A) and as a percentage of their maximal effect (FIG. 9B) showed that the differential sensitivities to the respective growth factors were approximately the same as those observed for burst-component colonies, both for the proportional and the plateau components of the curves. From the actual numbers obtained in all these experiments we calculated the number of burst-component colonies per burst both at the background level of retinoids (i.e. in the absence of both IGF-I and Epo, or at their ineffective concentrations), and at their plateau levels. The value of background averaged 1.7 colonies (with $\geq 50$ cells each) per burst (77 colonies per 42 bursts/$10^5$ MNC); the values at plateau averaged 4 colonies per burst (467 colonies per 116 bursts) at maximal IGF-I stimulation and 5.4 colonies per burst (488 colonies per 91 bursts) at maximal Epo stimulation. This shows that one of the actions common to both growth factors is to enhance the proliferation of BFU-E-derived progenitors within each burst.

EXAMPLE 7

Effect of Anti-Epo Antibody

These experiments showed, under optimal conditions, that IGF-I can substitute for Epo in the production of erythroid bursts. An investigation was conducted to determine whether erythroid bursts would develop under the influence of IGF-I in the presence of antibody directed against Epo. In FIG. 10, bar 1 shows the number of bursts obtained in the full SF medium but lacking IGF-I, with 6.0 U/mL of Epo. Comparison with bar 4, in which anti-Epo antibody was added to the same medium containing Epo, shows that the antibody was effective in inhibiting burst formation that was dependent on Epo. Bar 3 shows that burst formation under the influence of IGF-I was not affected by the same anti-Epo antibody. Similar results were obtained when the day-14 cultures were scored for burst-component colonies. This conclusively demonstrates that the production of erythroid bursts under the influence of IGF-I does not occur through an Epo-dependent mechanism. Bars 4 and 5 show that in this SF medium a limited number of bursts form which do not require either Epo or IGF-I, and the anti-Epo antibody has no effect on their development. Evidently, the presence of IL-3, hemin and retinyl acetate or all-trans-retinoic acid is sufficient to support the production of these "Epo- and IGF-I-independent bursts".

EXAMPLE 8

Role of Accessory Cells in Burst Production in An Improved SF Medium

The experiments described thus far were done with Ficoll-Hypaque density gradient-separated cells, and they provided information on the growth factor requirements of human erythroid progenitors among PB MNC, against a SF background. To find out whether or not accessory cells play a role under these conditions, we removed plastic adherent cells. FIG. 11 shows that production of erythroid bursts could be completely eliminated by this procedure, despite the presence of IL-3, hemin, retinyl acetate, Epo and IGF-I at what would otherwise be optimal concentrations. Thus accessory cells clearly still play a crucial role in the production of erythroid bursts by PB MNC in the improved SF medium.

EXAMPLE 9

Effect of Recombinant Human Stem Cell Growth Factor as a Replacement for Adherent Cells Recombinant human (rHu) SCF was added to the SF cultures of Ficoll-Hypaque density gradient separated MNC which had been exposed to 1.5 hours' adherence to plastic.

Figure 12A:
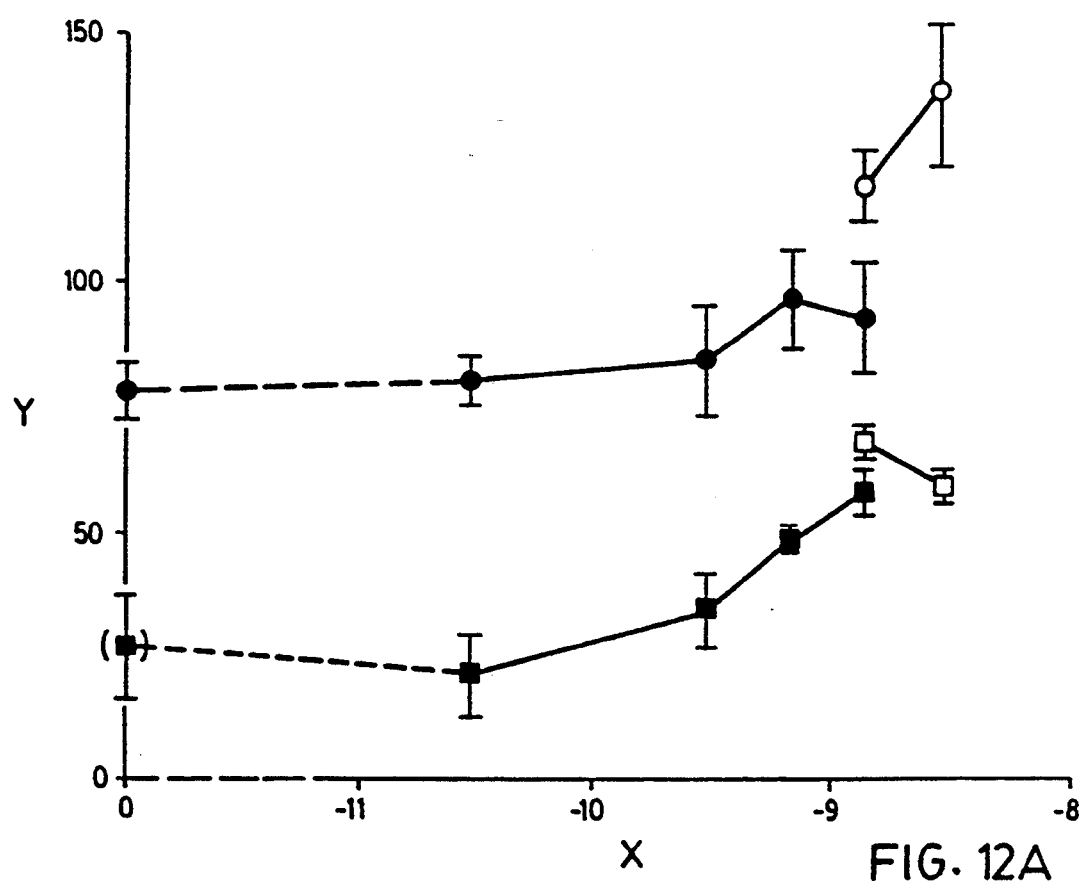
Figure 12B:
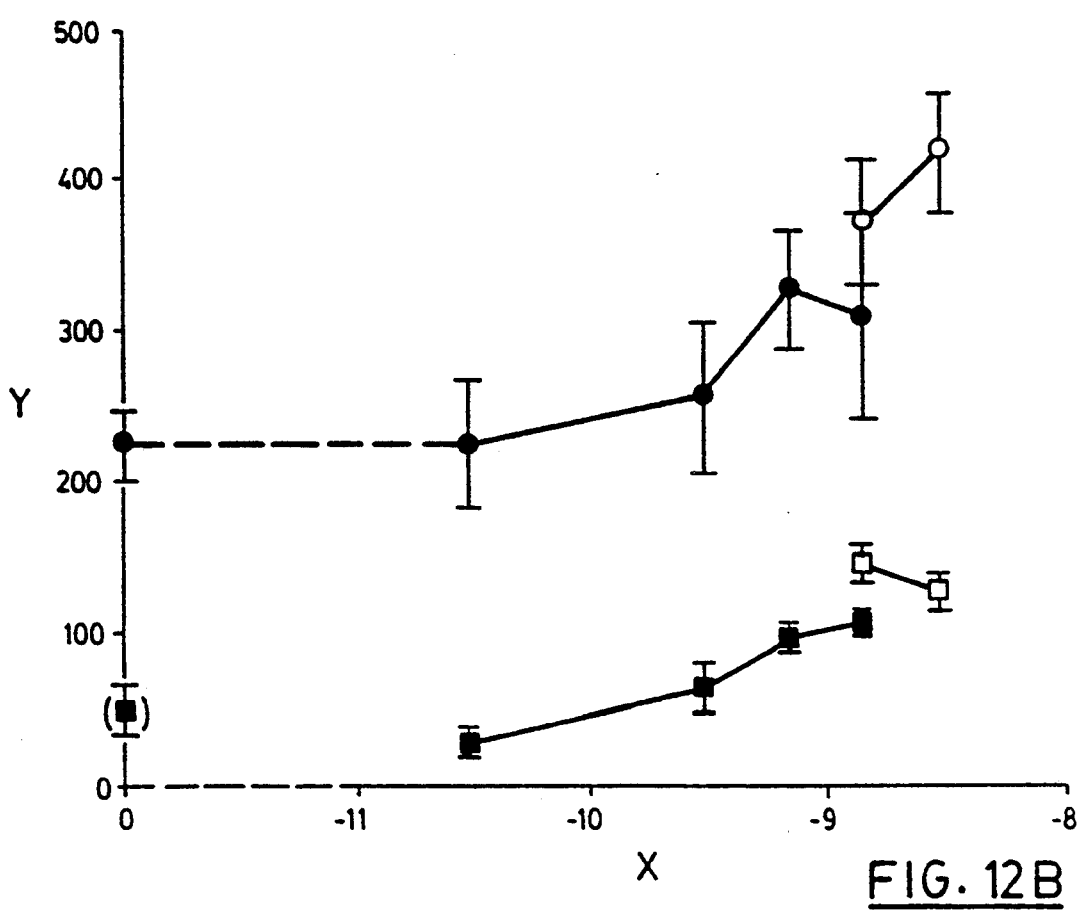

When the rHu SCF was added to cultures of untreated PB MNC under SF conditions at concentrations ranging from 30 to 1500 pM (1 to 50 ng/mL) in the absence of IL-3, they showed virtually no change in the number of bursts (FIG. 12A closed circles) or of burst-component colonies (BCC) (FIG. 12B, closed circles). In the presence of 0.8 nM rHu IL-3, no significant increase ($t=2$, with 2 df and $p>0.1$) in burst-formation was observed at 1.5 nM rHu SCF (FIG. 12A open circles). In contrast, adherent celldepleted PB MNC showed a significant increase of burst- and BCC-formation upon the addition of as little as 30 pM rHu SCF (FIGS. 12A and 12B, closed squares), but no increase upon the addition of IL-3 (in the presence of hemin and 1.5 or 3.0 nMrHu SCF). The control point shown in parentheses (closed squares at 0 rHu SCF in FIG. 12B) represents erythroid colonies with $<50$ cells (an average of 25) which are promoted by the BPA-like action of hemin alone and were tentatively grouped as clusters, possibly equivalent to undeveloped bursts (FIG. 12A, closed square in parentheses). Some of these small hemin-dependent colonies approached the 50-cell size, and the effect of rHu SCF, under these conditions (in the absence of IL-3), was to increase the cellularity (up to 200 cells) of the BCC; it also rendered the colonies rounder and more compact. It thus allowed full burst development.

Figure 12C:
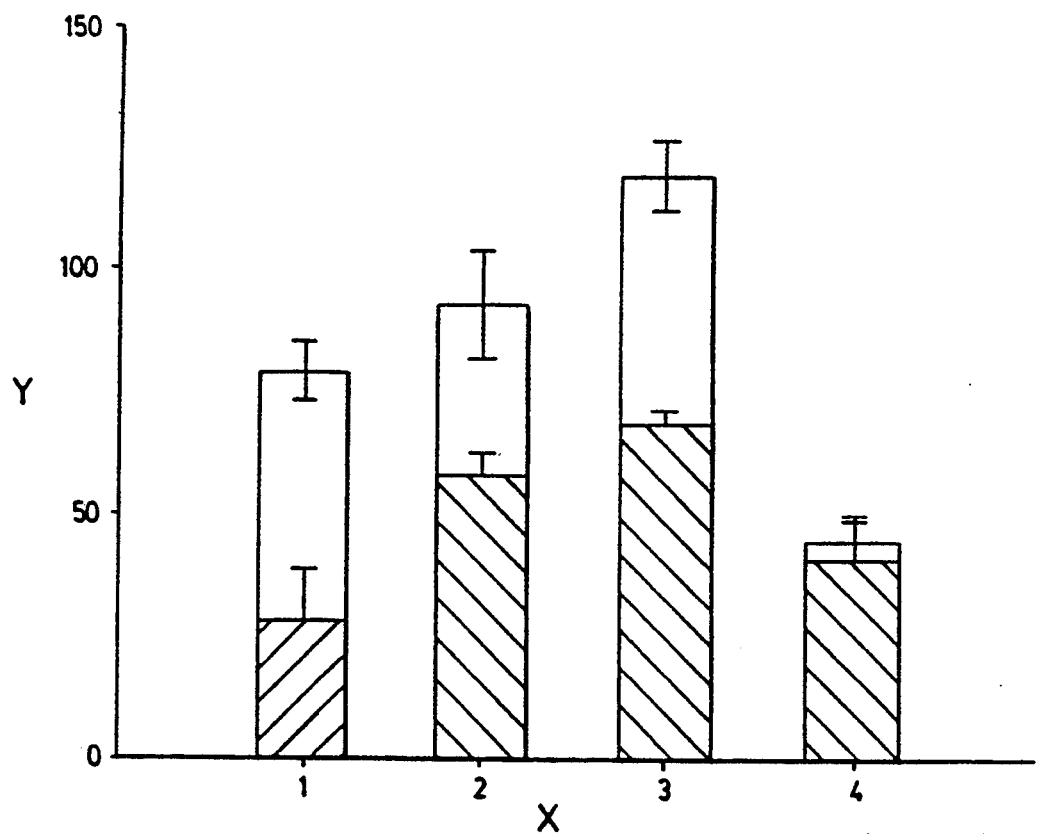
Figure 12D:
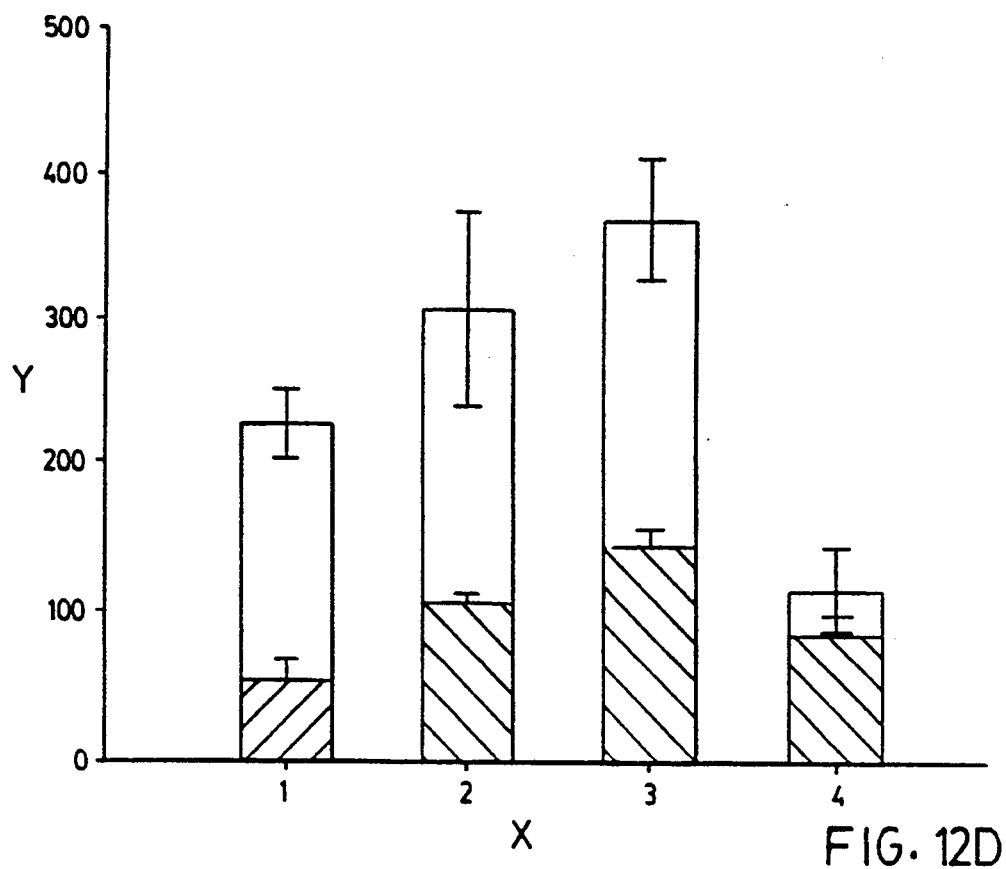

A comparison of the effects of rHu SCF and of the two defined BPA-like activities used in our SF medium (28), hemin and rHu IL-3, upon burst-formation shows that optimal conditions for burst-formation appeared to require the presence of all three factors, rHu IL-3, rHu SCF and hemin (FIG. 12C, open bar 3), even though the addition of rHu IL-3 to both hemin and rHu SCF did not significantly increase the number of BCC observed (cf open bars 2 and 3, FIG. 12D). Removal of adherent cells appeared to prevent the capacity of hemin to promote erythroid colonies large enough for them to be classified as BCC; the number of erythroid colonies with 20 to 50 hemoglobinized cells (FIG. 12D, striped bar 1) and of "undeveloped bursts" (FIG. 12C, striped bar 1) were fewer than the number of BCC and bursts formed in the absence of hemin (FIGS. 12C and 12D, closed bars 4). Finally, addition of rHu IL-3 to a combination of hemin and rHu SCF did not significantly increase the number of bursts obtained with hemin and rHu SCF alone (cf closed bars 2 and 3, FIG. 12C) and only marginally increased the number of BCC obtained with hemin and rHu SCF (cf closed bars 2 and 3, FIG. 12D).

EXAMPLE 10

Effect of Proliferation-Promoting Growth Factors (Hemin, rHu-IL-3 and rHu SCF) upon Multi-lineage Hematopoietic Colonies from Human Bone-Marrow Normal bone-marrow mononuclear cells (BM MNC) separated and washed as described in Materials and Methods for PB MNC were grown in the basal serum-free medium, together with 3.0 u/mL of rHu Epo, $3 \times 10^{-8}$M rHu IGF-1 and $3 \times 10^{-8}$ retinyl acetate, with different combinations of proliferation-stimulatory activities (250 µM Hemin, 10 ng/mL rHu IL-3 and 50 ng/mL rHu SCF). Hemin is necessary to detect both erythroid (CFU-E- and BFU-E-derived) and non-erythroid (CFU-GM-derived) colonies (FIG. 13 bars 1), but the numbers of these colonies are significantly increased by the addition of rHu IL-3 (bars 2). The addition of rHu SCF in the absence of rHu IL-3 further increased the levels of these colonies over those obtained with rHu IL-3 in the absence of rHu SCF (CP. bars 3 and 2), and expression of multi-lineage CFU-GEMM-derived colonies could be observed under these conditions (Cp. open bar 3). Lastly, optimal levels of all four types of colonies were obtained when Hemin, rHu IL-3 and rHu SCF were all added together, making the medium complete (bars 4).

Results shown in FIG. 14 were obtained using human bone-marrow mononuclear progenitor cells from patients with Diamond Blackfan Anemia (DBA). Bars 1 of FIG. 14 are comparable to bars 1 of FIG. 13 as obtained under the same culture conditions (complete medium minus rHu IL-3 and rHu SCF). Bars 2 of FIG. 14, however, show that DBA patients have dramatically fewer CFU-E (late erythroid progenitors) and BFU-E (early erythroid progenitors) than normals do (CP bars 3 of FIG. 13) when rHu SCF is added to Hemin in the absence of rHu IL-3. Finally, the addition of rHu IL-3 to Hemin in the absence of rHu SCF (FIG. 14, bars 3) exhibited the same greatly diminished expression of erythroid bone-marrow progenitors in DBA but it also indicates a greater expression of non-erythroid (CFU-GM) progenitors in DBA than in normals (CP. open bar 3 from FIG. 14 with the more densely stippled bar 2 of FIG. 13).

EXAMPLE 11

Erythroid Colony Formation by Polycythemia Vera Primary and Continuous Cell Populations in an Improved SF Medium FIG. 15 shows the cell-dose response curve for burst-formation by PB MNC from a Polycythemia vera (PV) patient in our novel SF medium, without rHu SCF (closed circles) and without both rHu SCF and rHu Epo (stippled circles). In both instances, the medium contained 10 ng/mL rHu IL-3, 0.25 mM Hemin, $3 \times 10^{-8}$M retinyl acetate and $3 \times 10^{-8}$M rHu IGF-1. Where indicated rHu Epo was employed at 3 U/mL. Either curve of FIG. 15 extrapolates through points not significantly different from the origin, indicating that, with or without rHu Epo, our novel SF medium is performing satisfactorily for burst-formation by PV PB MNC.

The improved SF medium performs equally well for an analysis of "CFU-E-like" and "BFU-E-like" erythroid colonies obtained from an immortalized cell line isolated from the peripheral blood of another PV patient, as is shown by the two curves of FIG. 16, one for day 7 erythrocytic-like colonies (open circles) and the other for day-14 burst-like colonies (closed circles).

EXAMPLE 12

Presumed Autocrine Growth of a Bi-Phenotypic Leukemia Cell Line in SF Medium A bi-phenotypic leukemia cell line (B-1) from a patient with ALL (Acute Lymphoblastic Leukemia) was studied for its growth characteristics in our novel SF medium. Growth could be detected with the basal SF medium alone (in the absence of all peptide growth factors, namely rHu IL-3, rHu SCF, rHu EPO and rHu IGF-1, as well as in the absence of Hemin and retinoids), as shown in bar 2 of FIG. 17A. Subtraction of d-α-tocopherol from the basal SF medium significantly diminished the viability of those biphenotypic leukemic cell day-9 colonies (bar 1, FIG. 17A) whereas addition of retinyl acetate further increased their growth (bar 3, FIG. 17A). These results indicate that B-1 cells can grow in the basal SF medium alone, in the absence of any growth-stimulating activities, presumably by means of an autocrine mechanism.

It is likely that this mechanism involves the secretion of IGF-1 by these cells, inasmuch as the addition of IGF-1 alone to the basal SF medium nearly tripled the number of B-1 colonies (of bars 2 and 1 of FIG. 17B).

REFERENCES

1. Kanamura A, Okamoto T, Hara H, Nagai K: Developmental Changes in Erythropoietin Responsiveness of Late Erythroid Precursors in Mouse Hemopoietic Organs. Dev Biol 92:221, 1982
2. Beckman B, Belegu RD, Belegu M, Katsuoka Y, Fisher JW: Hypoxic Enhancement of Murine Erythroid Colony Formation, in Baum, Ledney, Thierfelder (eds): Experimental Hematology Today, New York, S. Karger, 1982, p 53.
3. Kurtz A, Hart W, Jelkmann W, Zapf J, Bauer C: Activity in Fetal Bovine Serum That Stimulates Erythroid Colony Formation in Fetal Mouse Livers is Insulin-like Growth Factor Int J Clin Invest 76:1643, 1985
4. Kurtz A, Jelkmann W, Bauer C: A New Candidate For The Regulation of Erythropoiesis: Insulin-like Growth Factor I. FEBS 149:105, 1982.
5. Akahane K, Tojo A, Urabe A, Takaku F: Pure Erythropoietic Colony and Burst Formations in Serum-Free Culture and Their Enhancement By Insulin-like Growth Factor I. Exp Hematol 15:197, 1987.
6. Stewart S, Zhu B-D, Axelrad AA: A "Serum-Free" Medium For The Production of Erythropoietic Bursts By Murine Bone Marrow Cells. Exp Hematol 12:309, 1984.
7. Dainiak N, Kreczko S, Cohen A, Pannell R, Lawler J: Primary Human Marrow Cultures For Erythroid Bursts in Serum-Substituted Culture. Exp Hematol 12:309, 1985.
8. Porter PN, Ogawa M: Erythroid Burst-Promoting Activity (BPA), in Dunn CDR (ed): Current Concepts in Erythropoiesis, New York, John Wiley & Sons Ltd., 1983, p 81.
9. Sonoda Y, Yang Y-C, Wong GG, Clark SC, Ogawa M: Erythroid Burst-Promoting Activity of Purified Recombinant Human GM-CSF and Interleukin-3: Studies With Anti-GM-CSF and Anti-IL-3 Sera and Studies in Serum-Free Cultures. Blood 72:1381, 1988.

10. Konwalinka G, Geissler D, Peschel C, Breier C, Grunewald K, Odavic R, Braunsteiner H: Human Erythropoiesis In Vitro And The Source of Burst-Promoting Activity in a Serum-Free System. Exp Hematol 14:899, 1986.

11. Migliaccio G, Migliaccio AR: Cloning of Human Erythroid Progenitors (BFU-E) in the Absence of total Bovine Serum. Br J Haematol 67:129, 1987.

12. Migliaccio G, Migliaccio AR, Adamson JW: In Vitro Differentiation of Human Granulocyte/Macrophage and Erythroid Progenitors: Comparative Analysis of the Influence of Recombinant Human Erythropoietin, G-CSF, GM-CSF, and IL-3 In Serum-Supplemented and Serum-Deprived Cultures. Blood 72:248, 1988.

13. Misago M, Chiba S, Kikuchi M, Tsukada J, Sato T, Oda S, Eto S: Effect of Recombinant Human Interleukin 3, Granulocyte-Macrophage Colony-Stimulating Factor and Granulocyte Colony-Stimulating Factor on Human BFU-E In Serum-Free Cultures Intl J Cell Cloning 7:37, 1989

14. Konwalinka G, Breier C, Geissler D, Peschel C, Wiedermann CJ, Patsch J, Braunsteiner H: Proliferation and Differentiation of Human Erythropoiesis In Vitro: Effect of Different Lipoprotein Species. Exp Hematol 16:125, 1988.

15. Porter PN, Ogawa M: Characterization of Human Erythroid Burst-Promoting Activity Derived From Bone Marrow Conditioned Media. Blood 59:1207, 1982.

16. Linch DC, Lipton JM, Nathan DG: Identification of Three Accessory Cell Populations in Human Bone Marrow With Erythroid Burst-Promoting Properties. J Clin Invest 75:1278, 1985.

17. Dukes PP, Ma A, Clemons GK, Meytes D: Measurement of Human Erythroid Burst-Promoting Activity By a Specific Cell Culture Assay. Exp. Hematol 13:59, 1985.

18. Zsebo K, Martin F, Suggs S, Wypych J, Lu H, McNiece I et al (1990) Biological Characterization of a Unique Early Acting Hematopoietic Growth Factor. Exp Hematol 18:703 (abs).

19. Broxmeyer HE, Cooper S, Lyman SD, Williams DE (1990) Characteristics of a Murine Ligand for C-kit (MGF): A Stimulating/Enhancing Factor For Early Murine and Human Bone Marrow Hemopoietic Progenitor Cells. Blood 76:134a (abs).

20. Migliaccio G, Migliaccio AR, Valinsky K et al. (1990) Recombinant Rat Stem Cell Factor (rr SCF) Induces Proliferation and Differentiation of Primitive Hematopoietic Progenitor Cells (HPC) in Serum-Deprived Cultures. Blood 76:156a (abs).

21. McNiece I, Langley K, Zsebo K (1991) Recombinant Human Stem Cell Factor Synergises With GM-CSF, G-CSF, IL-3 and Epo to Stimulate Human Progenitor Cells of the Myeloid and Erythroid Lineages. Exp Hematol 19:226.

22. Anderson DM, Lyman SD, Baird A et al. (1990) Molecular Cloning of Mast Cell Growth Factor, A Hematopoietin That is Active in Both Membrane Bound and Soluble Forms. Cell 63:235.

23. Brox A, Congote F, Fauser AA: A Novel Peptide Stimulates In Vivo and In Vitro Erythropoiesis. Blood 74:14a, 1989 (abstr.).

24. DeLeenher AP, Lambert WC, Claeys I: All-trans retinoic Acid: Measurement of Reference Values in Human Serum By High Performance Liquid Chromatography. J Lipid Res 23:1362, 1982.

25. DeRuyter MG, Lambert WE, DeLeenher AP: Retinoic Acid: An Endogenous Compound of Human Blood. Unequivocal Demonostration of Retinoic Acid in Normal Physiological Conditions. Anal Biochem 98:402, 1979.

26. Douer D, Koeffler HP: Retinoic Acid Enhances Growth of Human Early Erythroid Progenitor Cells In Vitro. J. Clin. Invest 69:1039, 1982.

27. Correa, P. N., Axelrad, A. A.: Retinyl Acetate and All-Trans Retinoic Acid Enhance Erythroid Colony Formation By Circulating Humar Progenitors in a Complete Serum Free Medium. An Improved Serum-Free Medium. Int. J. Cell Cloning 10:286 (1992). 28. Correa P. N., Axelrad, A. A. Production of Erythropoietic Burst by Progenitor cells from Adult Human Peripheral Blood in an Improved Serum-Free Medium: Role of Insulinlike Growth Factor 1. Blood 78:2823 (1991).

What we claim is:

1. A basal serum-free medium for maintaining cells selected from the group consisting of hematopoietic stem cells, hematopoietic progenitor cells and leukemia cells, the medium consisting of:

a minimum essential medium;

from 1 μg/mL to 100 mg/mL of each of adenine deoxyriboside, thymine deoxyriboside, guanine deoxyriboside and cytosine deoxyriboside;

from 1 μg/mL to 100 mg/mL of each of adenine riboside, uridine riboside, guanine riboside and cytosine riboside;

from 0.1 mM to 20 mM final molarity of L-glutamine;

from 1 mg/mL to 100 mg/mL of an albumin which is deionized, fatty-acid free and globulin-free, and which is selected from the group consisting of bovine serum albumin, human serum albumin and recombinant albumin;

from 1 μg/mL to 1 mg/mL of a human or bovine transferrin;

from 0.1 μg/mL to 100 μg/mL of a phosphatidyl choline;

from 0.1 μg/mL to 100 μg/mL of a $C_{16}$-$C_{24}$ unsaturated fatty acid;

from 0.1 μg/mL to 100 μg/mL of a cholesterol;

from 1 μM to 1 mM final molarity of at least one bioacceptable antioxidant;

and from 0.1 μg/mL to 250 μg/mL of at least one antibiotic substance wherein (i) the medium is essentially free of burst promoting activity, and (ii) the cells do not proliferate in the medium.

2. The basal serum-free medium of claim 1 wherein the phosphatidyl choline is synthetic L-α-phosphatidyl choline dipalmitoyl.

3. The basal serum-free medium of claim 2 wherein the unsaturated fatty acid is linoleic acid or oleic acid.

4. The basal serum-free medium of claim 3 wherein the cholesterol is porcine liver cholesterol.

5. The basal serum-free medium of claim 4 wherein the antioxidant is selected from the group consisting of β-mercaptoethanol, α-thioglycerol and combinations thereof.

6. The basal serum-free medium of claim 5 wherein the antibiotic substance is selected from the group consisting of sodium penicillin G, streptomycin sulphate and combinations thereof.

7. The basal serum-free medium of claim 6 further including from 0.1 mg/mL to 10 mg/mL of a bioacceptable semi-solid or viscous matrix material selected from the group consisting of methylcellulose, agar and agarose.

8. A serum-free culture medium for the growth and differentiation of cells selected from the group consisting of hematopoietic stem cells, hematopoietic progenitor cells, and leukemia cells, whereby said medium is free from indigenous cell growth factors and consists of:
   (a) a basal serum-free medium as defined in claim 1;
   (b) at least one growth-promoting agent selected from the group consisting of heme or hemin in an amount of from 50 $\mu$M to 1 $\mu$mM, interleukin-3 in an amount from 0.1 ng/mL to 1 $\mu$g/mL, and recombinant human stem cell factor in an amount from 0.5 ng/mL to 1 $\mu$g/mL; and
   (c) at least one cell differentiation-promoting agent selected from the group consisting of erythropoietin in an amount of from 0.1 ng/mL to 1 $\mu$g/mL, insulin-like growth factor in an amount from 1 pg/mL to 1 $\mu$g/mL, and a retinoid in an amount from 0.1 nM to 0.1 mM.

9. The culture medium of claim 8 wherein the cell differentiation promoting agent is erythropoietin.

10. The culture medium of claim 9 wherein the growth promoting agent is interleukin-3.

11. The culture medium of claim 10 wherein the growth promoting agent is recombinant human stem cell factor.

12. The culture medium of claim 11 which includes insulin-like growth factor 1.

13. The culture medium 12 which includes hemin as the growth promoting agent.

14. The culture medium of claim 13 which includes a retinoid selected from the group consisting of retinoic acid and lower alkyl esters of retinoic acid.

15. The culture medium of claim 14 wherein the retinoid is retinyl acetate.

16. The culture medium of claim 14 wherein the retinoid is all-trans retinoic acid.

17. The culture medium of claim 16 wherein the basal serum-free medium consists of:
   a minimum essential medium;
   from 1 $\mu$g/mL to 100 mg/mL of each of adenine deoxyriboside, thymine deoxyriboside, guanine deoxyriboside and cytosine deoxyriboside;
   from 1 $\mu$g/mL to 100 mg/mL of each of adenine riboside, uridine riboside, guanine riboside and cytosine riboside;
   from 0.1 mM to 20 mM final molarity of L-glutamine;
   from 1 mg/mL to 1 mg/mL of an albumin which is deionized, fatty-acid free and globulin-free, and which is selected from the group consisting of bovine serum albumin., human serum albumin and recombinant albumin;
   from 1 $\mu$g/mL to 1 mg/mL of a human or bovine transferrin;
   from 0.1 $\mu$g/mL to 100 $\mu$g/mL of synthetic L-$\alpha$-phosphatidyl choline dipalmitoyl;
   from 0.1 $\mu$g/mL to 100 $\mu$g/mL of a $C_6$-$C_{24}$ unsaturated fatty acid selected from the group consisting of linoleic acid, oleic acid and combinations thereof
   from 0.1 $\mu$g/mL to 100 $\mu$g/mL of a cholesterol;
   from 1 $\mu$M to 1 mM final molarity of at least one bioacceptable antioxidant selected from the group consisting of $\beta$-mercaptoethanol, $\alpha$-thioglycerol and combinations thereof; and
   from 0.1 $\mu$g/mL to 250 $\mu$g/mL of at least one antibiotic substance selected from the group consisting of sodium penicillin G, streptomycin sulphate and combinations thereof.

18. The culture medium of claim 16 wherein the basal serum-free medium consists of:
   a minimum essential medium;
   from 1 $\mu$g/mL to 100 mg/mL of each of adenine deoxyriboside, thymine deoxyriboside, guanine deoxyriboside and cytosine deoxyriboside;
   from 1 $\mu$g/mL to 100 mg/mL of each of adenine riboside, uridine riboside, guanine riboside and cytosine riboside;
   from 0.1 mM to 20 mM final molarity of L-glutamine
   from 1 mg/mL to 100 mg/mL of an albumin which is deionized, fatty-acid free and globulin-free, and which is selected from the group consisting of bovine serum albumin, human serum albumin and recombinant albumin;
   from 1 $\mu$g/mL to 1 mg/mL of a human or bovine transferrin;
   from 0.1 $\mu$g/mL to 100 $\mu$g/mL of synthetic L-$\alpha$-phosphatidyl choline dipalmitoyl;
   from 0.1 $\rho$g/mL to 100 $\mu$g/mL of a $C_{16}$-$C_{24}$ unsaturated fatty acid selected from the group consisting of linoleic acid, oleic acid and combinations thereof;
   from 0.1 $\mu$g/mL to 100 $\mu$g/mL of a cholesterol;
   from 1 $\mu$M to 1 mM final molarity of at least one bioacceptable antioxidant selected from the group consisting of $\beta$-mercaptoethanol, $\alpha$-thioglycerol and combinations thereof;
   from 0.1 $\mu$g/mL to 250 $\mu$g/mL of at least one antibiotic substance selected from the group consisting of sodium penicillin G, streptomycin sulphate and combinations thereof; and
   from 0.1 mg/mL to 10 mg/mL of a bio-acceptable semi-solid or viscous matrix material selected from the group consisting of methylcellulose, agar and agarose.

19. The basal serum-free medium of claim 1 further including from 100 nM to 1 mM of d-$\alpha$-tocopherol or an ester thereof.

* * * * *

UNITED STATES PATENT AND TRADEMARK OFFICE
CERTIFICATE OF CORRECTION

PATENT NO. : 5,397,706  Page 1 of 3
DATED : March 14, 1995
INVENTOR(S) : Paulo N. CORREA and Arthur A. AXELRAD It is certified that error appears in the above-indentified patent and that said Letters Patent is hereby corrected as shown below:

On the title page, item: [76] Inventor: change "Arthur A. Alexrad, 3 Troon Court, Willowdale, Ontario, Canada, M2P 1N4" to -- Arthur A. Axelrad, #1 Concorde Place, Suite 1903, Toronto, Ontario, Canada M3C 3K6--.

Column 10, line 9, change "Serum" to --Serum-Free--;
              line 50, change "Linenbeld" to --Lunenfeld--.
    Column 11, line 4, change "cor" to --for--;
              line 24, delete "growth", first occurrence;
              line 25, insert --growth-- before "of".
    Column 12, line 53, change "erythireporetic" to --erythropoietic--.
    Column 13, line 19, change "burst/1,300/PB/MNC" to --burst/1,300 PB/MNC--;
              line 24, change "Required" to --Requirement--.
    Column 16, line 26, change "celldepleted" to --cell-depleted--.

UNITED STATES PATENT AND TRADEMARK OFFICE
CERTIFICATE OF CORRECTION

PATENT NO. : 5,397,706
DATED : March 14, 1995
INVENTOR(S) : Paulo N. CORREA and Arthur A. AXELRAD It is certified that error appears in the above-indentified patent and that said Letters Patent is hereby corrected as shown below:

Column 17, line 4, change "rHu-IL-3" to --rHu IL-3--;
line 21, change "CP." to --cf--;
line 24, change "Cp." to --cf--;
line 36, change "CP" to --cf--;
line 43, change "CP." to --cf--.

Column 18, line 2, change "circles" to --squares--;
line 27, change "of", second occurrence, to --cf--;
line 43, delete "Int".

Column 19, line 8, change "total" to --Fetal--.

Column 20, line 3, change "Demonostration" to --Demonstration--;
line 11, change "Humar" to --Human--;
line 12, delete "An Improved";
line 13, delete "Serum-Free Medium.";
line 14, delete "28. Correa P. N., Axelrad, A. A. Production" and insert on a new line --28. Correa P. N., Axelrad, A. A. Production--;

UNITED STATES PATENT AND TRADEMARK OFFICE
CERTIFICATE OF CORRECTION

PATENT NO. : 5,397,706
DATED : March 14, 1995
INVENTOR(S) : Paulo N. CORREA and Arthur A. AXELRAD It is certified that error appears in the above-indentified patent and that said Letters Patent is hereby corrected as shown below:

line 15, change "Burst" to --Bursts--, and "cells" to --Cells--.

Signed and Sealed this

Twenty-first Day of May, 1996

Attest:

BRUCE LEHMAN

Attesting Officer  Commissioner of Patents and Trademarks